(12) United States Patent
Lagrange et al.

(10) Patent No.: US 7,282,068 B2
(45) Date of Patent: Oct. 16, 2007

(54) POLYCATIONIC AZO COMPOUNDS FOR DYEING KERATIN FIBERS, DYE COMPOSITION CONTAINING THE SAME, AND METHODS FOR MAKING SUCH COMPOUNDS

(75) Inventors: Alain Lagrange, Coupvray (FR);
Hervé David, Joinville le Pont (FR);
Andrew Greaves, Montevrain (FR)

(73) Assignee: L'Oreal S.A., Paris (FR)

( * ) Notice: Subject to any disclaimer, the term of this patent is extended or adjusted under 35 U.S.C. 154(b) by 281 days.

(21) Appl. No.: 11/139,626

(22) Filed: May 31, 2005

(65) Prior Publication Data

US 2006/0021160 A1    Feb. 2, 2006

Related U.S. Application Data

(60) Provisional application No. 60/588,037, filed on Jul. 15, 2004.

(30) Foreign Application Priority Data

May 28, 2004 (FR) .................................. 04 05805

(51) Int. Cl.
*A61K 7/13* (2006.01)
(52) U.S. Cl. .................. 8/405; 8/406; 8/407; 8/408; 8/409; 8/410; 8/411; 8/412; 8/421; 8/423; 8/426; 8/437; 8/454; 8/565; 8/566; 8/567; 8/568; 8/570; 8/573; 8/606; 8/616; 548/268.8; 548/300.1; 548/356.1; 546/184; 546/251
(58) Field of Classification Search .................. 8/405, 8/406, 407, 408, 409, 410, 411, 412, 421, 8/423, 426, 437, 454, 565, 566, 567, 568, 8/570, 573, 606, 616; 548/268.8, 300.1, 548/356.1; 546/184, 251
See application file for complete search history.

(56) References Cited

U.S. PATENT DOCUMENTS

| | | | |
|---|---|---|---|
| 4,003,699 A | 1/1977 | Rose et al. | |
| 4,823,985 A | 4/1989 | Grollier et al. | |
| 5,061,289 A | 10/1991 | Clausen et al. | |
| 5,380,340 A | 1/1995 | Neunhoeffer et al. | |
| 5,534,267 A | 7/1996 | Neunhoeffer et al. | |
| 5,663,366 A | 9/1997 | Neunhoeffer et al. | |
| 5,708,151 A * | 1/1998 | Mockli | 534/608 |
| 5,766,576 A | 6/1998 | Löwe et al. | |
| 6,099,592 A | 8/2000 | Vidal et al. | |
| 6,284,003 B1 | 9/2001 | Rose et al. | |
| 6,730,789 B1 | 5/2004 | Birault et al. | |

FOREIGN PATENT DOCUMENTS

| | | |
|---|---|---|
| DE | 23 59 399 A1 | 6/1975 |
| DE | 38 43 892 A1 | 6/1990 |
| DE | 41 33 957 A1 | 4/1993 |
| DE | 195 43 988 A1 | 5/1997 |
| EP | 0 714 954 B1 | 6/1996 |
| EP | 0 770 375 A1 | 5/1997 |
| FR | 2 586 913 | 3/1987 |
| FR | 2 733 749 | 11/1996 |
| FR | 2 801 308 | 5/2001 |
| GB | 1 026 978 | 4/1966 |
| GB | 1 153 196 | 5/1969 |
| JP | 2-19576 | 1/1990 |
| WO | WO94/08969 | 4/1994 |
| WO | WO94/08970 | 4/1994 |
| WO | WO95/01772 | 1/1995 |
| WO | WO95/15144 | 6/1995 |
| WO | WO96/15765 | 5/1996 |
| WO | WO 02/100365 A1 | 12/2002 |
| WO | WO 03/029359 A1 | 4/2003 |

OTHER PUBLICATIONS

STIC Search Report dated Apr. 25, 2007.*
French Search Report for FR 04 05805, dated Jan. 4, 2005, Examiner D. Voylazoglou.
English language Derwent Abstract of EP 0 770 375 A1, May 2, 1997.
English language abstract of JP 2-19576, Feb. 23, 1990.

* cited by examiner

*Primary Examiner*—Eisa Elhilo
(74) *Attorney, Agent, or Firm*—Finnegan, Henderson, Farabow, Garrett & Dunner LLP

(57) ABSTRACT

The present disclosure relates to compounds used as direct dyes, and dyeing compositions comprising such compounds. The disclosed compounds have the formula A-L-B, wherein A and B are chosen from arylazoimidazolium coloring functional groups, and L is a linker comprising at least one cationic group C. The disclosure also relates methods of using such compositions for coloring keratin fibers, such as the hair.

55 Claims, No Drawings

POLYCATIONIC AZO COMPOUNDS FOR DYEING KERATIN FIBERS, DYE COMPOSITION CONTAINING THE SAME, AND METHODS FOR MAKING SUCH COMPOUNDS

This application claims benefit of U.S. Provisional Application No. 60/588,037, filed Jul. 15, 2004, the contents of which are incorporated herein by reference. This application also claims benefit of priority under 35 U.S.C. § 119 to French Patent Application No. 04 05805, filed May 28, 2004, the contents of which are also incorporated by reference.

The present disclosure relates to polycationic azo compounds and their use as direct dyes in compositions for dyeing keratin fibers such as human hair. This disclosure also relates to dye compositions containing these direct dyes, and to methods for dyeing keratin fibers using these compositions.

It is known practice to dye keratin fibers, such as human hair, with dye compositions containing oxidation dye precursors. These dye precursors are generally known as oxidation bases, and include, for example, compounds such as ortho- or para-phenylenediamines, ortho- or para-aminophenols, and heterocyclic compounds. These oxidation bases are colorless or weakly colored compounds that, when combined with oxidizing products, may give rise to colored compounds (dyes) by oxidative condensation. These dyes are insoluble in the dyeing medium and are trapped within the hair.

Further it is known that various color shades may be obtained by combining the above oxidation bases with couplers or coloration modifiers. Examples of coloration modifiers include but are not limited to aromatic meta-diamines, meta-aminophenols, meta-diphenols, and certain heterocyclic compounds, for example, indole compounds. The variety of molecules used as oxidation bases and couplers allows a wide range of color shade to be obtained.

The "permanent" coloration obtained from the above described dyes must satisfy a number of requirements. For example, the dyes must have no negative toxicological effects, and be able to produce shades in the desired intensity. Further, the dyes must exhibit good resistance to external agents such as light, bad weather, washing, permanent-waving, perspiration and rubbing.

In addition, the dyes must be able to cover grey hair, and should be as unselective as possible. By "unselective," it is meant that the dyes should produce the smallest possible differences in coloration along the same keratin fiber, although the fiber may be differently sensitized (i.e. damaged) between its end and its root.

The dyeing of keratin fibers with a direct or semi-permanent dye is also known. A direct dye is a colored or coloring molecule having affinity for the fibers. The process for dyeing fibers with these dyes is known as direct dyeing, and comprises applying one or more direct dyes to keratin fibers, leaving the direct dyes on the fibers to allow them to penetrate into the hair by diffusion, and then rinsing the fibers.

In contrast with oxidation dye compositions, direct or semi-permanent dye compositions may be used without the presence of an oxidizing agent. As a result, a keratin fiber may be repeatedly dyed with a direct or semi-permanent dye without damage.

For example, nitrobenzene, anthraquinone, nitropyridine, azo, xanthene, acridine, azine triarylmethane direct dyes are known in the art to be useful for dyeing keratin fibers.

However, dyeing of keratin fibers with direct dyes results in only temporary or semi-permanent coloration of the fiber. As a result of the nature of the bonds between the direct dyes and the keratin fiber, the dyes are easily desorbed from the surface and/or core of the fiber. Further, colorations obtained by direct dyeing generally show low dyeing power and poor fastness with respect to washing or perspiration. In addition, direct dyes are also generally sensitive to light. As a result, the resistance of the chromophore to photochemical attack may be poor, which leads to fading of the coloration over time.

Further, conventional direct dyes are not completely harmless.

As a result, direct dyes that are less harmful and that exhibit improved shampoo resistance and dye uptake are sought. The present disclosure relates to direct dyes and a dye compositions comprising direct dyes that exhibit these improvements.

For example, the present disclosure relates to direct dyes comprising polycationic azo compounds and the use of such dyes in dye compositions for dyeing keratin fibers. In addition to being less harmful then conventional direct dyes, keratin fibers which have been dyed with compositions containing the direct dyes of the present disclosure are resistant to external agents such as sunlight, bad weather, shampoo, and perspiration. Further, the dyes and dye compositions of the present disclosure allow strong, fast glints to be obtained on the fibers. Finally, the dyes and dye compositions of the present disclosure exhibit improved uptake, reduced selectivity, and a good toxicological profile.

One aspect of the present disclosure is a direct dye for use in a composition for dyeing keratin fibers such as human hair, wherein the direct dye includes a compound having the formula A-L-B. A and B are chosen from arylamidazolium coloring functional groups, and L comprises a linker comprising at least one cationic group C. Another aspect of the present disclosure is a method for manufacturing a dye composition comprising such a direct dye.

A further aspect of the disclosure is a dye composition for dyeing keratin fibers such as hair, comprising, in a medium that is suitable for dyeing, at least one compound of formula A-L-B as described above, and at least one oxidation base and/or at least one additional direct dye.

Yet another aspect of the disclosure relates to a process for dyeing keratin fibers such as hair, using compounds of formula A-L-B.

An additional aspect of the present disclosure is the use of a composition of the present disclosure on keratin fibers such as hair, so as to obtain dyeing results that exhibits good resistance to external agents and shampoos.

Other characteristics, aspects, subjects and advantages of the disclosure will become evident upon reading the description and the examples below.

In the formula A-L-B, A and B are independently chosen from a group containing an arylazomiidazolium coloring functionality bearing a cationic charge. The group L represents a "linker", which links together the groups A and B. The term "linker" means a linear or branched, saturated or unsaturated hydrocarbon-based chain, that may be terminated or interrupted with one or more carbonyl groups and/or one or more hetero atoms such as O, N or Si, or a chain comprising one or more aromatic rings or one or more aromatic or saturated heterocycles, wherein at least one cationic group C is intercalated in the chain. The cationic group(s) C may be intercalated at any point in the chain L, including at the ends of the chain. The bonding between the groups A and B and the group L may take place with any atom of the group L.

In one non-limiting embodiment, the compound of formula A-L-B comprises two groups containing a coloring functional group (dichromophore).

zolium and triazolium groups. In a non-limiting embodiment, the heterocyclic cationic group is an imidazolium group.

In another non-limiting embodiment, the aliphatic cationic groups may comprise divalent radicals having the formula —N$^+$—R$_1$R$_2$—, wherein R$_1$ and R$_2$ are independently chosen from C$_1$-C$_{10}$ alkyl, C$_1$-C$_{10}$ mono- and polyhydroxyalkyl radicals.

In a non-limiting embodiment, the cationic group C is chosen from aliphatic cationic groups and imidazolium, pyridinium and piperidinium groups.

In another non-limiting embodiment, the compound of formula A-L-B is chosen from compounds of formula (I) below:

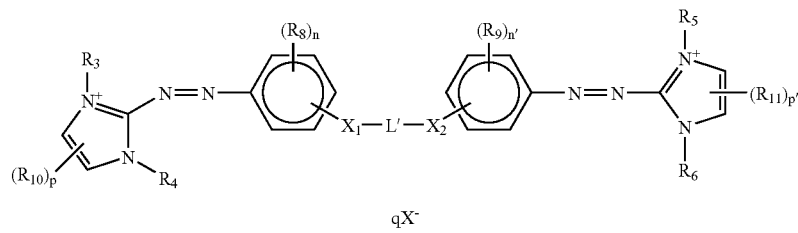

The linker may be chosen from linear and branched, saturated and unsaturated C$_1$-C$_{40}$, such as C$_1$-C$_{20}$, and C$_1$-C$_8$ hydrocarbon-based chains, wherein one or more of the carbon atoms of the chain may be replaced with hetero atoms, such as sulfur, nitrogen or oxygen; (hetero)arylene radicals; divalent terephthalamide radicals; divalent triazine radicals; or —NH—CO— radicals.

In a non-limiting embodiment, the chain constituting the linker may be substituted, for example, with a hydroxyl, an alkoxy such as a C$_1$-C$_6$ alkoxy, an amino or an alkylamino, such as a C$_1$-C$_6$ alkylamino, a radical or a halogen.

Examples of linkers include, but are not limited to alkylene radicals (C$_n$H$_{2n}$), including alkylene radicals containing from 1 to 6 carbon atoms, such as methylene, ethylene, propylene, etc.; (hetero)arylene radicals such as phenylene, naphthylene, phenanthrylene, triazinyl, pyrimidinyl, pyridyl, pyridazinyl and quinoxalinyl radicals; and alkyl-aryl-alkyl radicals.

Other non-limiting examples of suitable linkers include the triazines described in WO 03/029359, the alkylenes mentioned in U.S. Pat. No. 5,708,151, and the alkyl-aryl-alkyls mentioned in U.S. Pat. No. 5,708,151.

In a non-limiting embodiment, the linker L is a linear or branched C$_1$-C$_{20}$ hydrocarbon-based chain. In another non-limiting embodiment, the linker L is a C$_1$-C$_8$ hydrocarbon-based chain.

The cationic group C may be chosen from aliphatic and heterocyclic cationic groups.

Examples of heterocyclic cationic groups include, but are not limited to imidazolium, piperidinium, pyridinium, pyrawherein:

X$_1$ and X$_2$ are independently chosen from a piperazine ring substituted with C$_1$-C$_8$ alkyl radicals; radicals —O— and —NR$_7$—, where R$_7$ is a hydrogen atom, C$_1$-C$_8$ alkyl radicals and C$_1$-C$_8$ hydroxyalkyl radicals;

R$_3$, R$_4$, R$_5$, and R$_6$ are independently chosen from C$_1$-C$_8$ alkyl radicals and a C$_1$-C$_8$ hydroxyalkyl radical;

R$_8$ and R$_9$ are independently chosen from a hydrogen atom; C$_1$-C$_4$ alkyl radicals optionally substituted with one or more radicals chosen from hydroxyl, amino and C$_1$-C$_2$ (di)alkylamino radicals; carboxyl radicals; C$_1$-C$_2$ alkoxy radicals; amino radicals; C$_1$-C$_2$ (di)alkylamino radicals; and C$_2$-C$_4$ (poly)hydroxyalkylamino radicals;

R$_{10}$ and R$_{11}$ are independently chosen from a hydrogen atom; linear and branched C$_1$-C$_4$ alkyl radicals optionally substituted with one or more radicals chosen from hydroxyl, C$_1$-C$_2$ alkoxy, C$_2$-C$_4$ (poly)hydroxyalkoxy, amino, C$_1$-C$_2$ (di)alkylamino, carboxyl and sulfonic radicals; optionally substituted phenyl radicals; carboxyl radicals; and sulfonylamino radicals;

L' is a linker; and the group X$_1$-L'-X$_2$ (corresponding to the group L) comprises at least one cationic group C;

n and n' are integers ranging from 0 to 4;

p and p' are integers ranging from 0 to 2;

q is an integer ranging from 3 to 50, for example, from 3 to 10 or from 3 to 5; the value of q may be chosen so as to ensure that the compound of formula (I) is charge neutral;

X$^-$ is an anion of mineral or organic origin; X$^-$ may be chosen from halide ions, for example chloride and iodide; sulfate or hydrogen sulfate ions; and methosulfate, tosylate, carbonate, hydrogen carbonate, phosphate, nitrate and citrate ions.

In another non-limiting embodiment, the compound of formula A-L-B may be chosen from compounds having the following formulae:

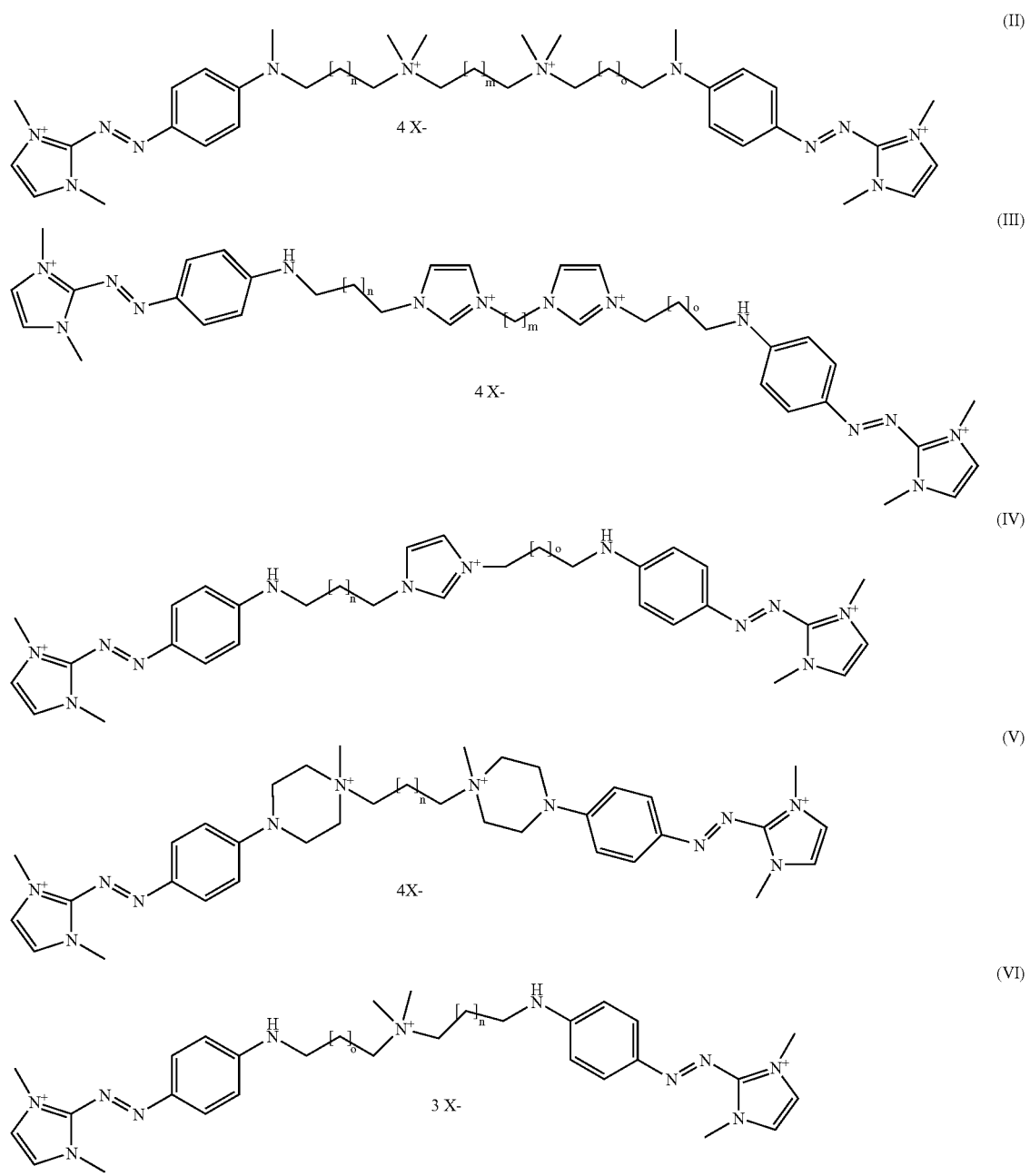

wherein:

X⁻ has the same meaning as disclosed for formula (I) above, and m and n are integers ranging from 0 to 20, such as from 0 to 8;

the value of m and n being such that the linker contains from 1 to 40, 1 to 20, or 1 to 8 carbon atoms.

The direct dyes having the formula A-L-B may be present in the disclosed dye composition in an amount ranging from 0.001% to 20%, from 0.01% to 10%, or from 0.1% to 5% by weight, relative to the total weight of the composition.

The dye composition of the present disclosure may further comprise one or more additional direct dyes other than the direct dyes of formula A-L-B described above. These additional direct dyes may be chosen from the direct dyes mentioned above, including, but not limited to neutral, acidic or cationic nitrobenzene dyes; neutral, acidic or cationic azo direct dyes; neutral, acidic or cationic quinone direct dyes such as anthraquinone direct dyes; azine direct dyes; triarylmethane direct dyes; indoamine direct dyes; and natural direct dyes. Dyes chosen from nitroaromatic dyes, anthraquinone dyes, naphthoquinone dyes, benzoquinone dyes, azo dyes, xanthene dyes, triarylmethane dyes, azine dyes, thiazine dyes, phenothiazine dyes, diazine dyes, phenodiazine dyes, acridine dyes, cyaninmethine dyes, azomethine dyes, nitro dyes, phthalocyanin dyes, indoaniline dyes, indophenol dyes and indoamine dyes and natural direct dyes may also be used.

Non-limiting examples of the aforementioned benzenic direct dyes that may be used according to the present disclosure include, but are not limited to the following compounds:

1,4-diamino-2-nitrobenzene;
1-amino-2-nitro-4-(β-hydroxyethylamino)benzene;
1-amino-2-nitro-4-bis(β-hydroxyethyl)aminobenzene;
1,4-bis(β-hydroxyethylamino)-2-nitrobenzene;
1-β-hydroxyethylamino-2-nitro-4-bis(β-hydroxyethylamino)benzene;
1-β-hydroxyethylamino-2-nitro-4-aminobenzene;
1-β-hydroxyethylamino-2-nitro-4-(ethyl)(β-hydroxyethyl)aminobenzene;
1-amino-3-methyl-4-β-hydroxyethylamino-6-nitrobenzene;
1-amino-2-nitro-4-β-hydroxyethylamino-5-chlorobenzene;
1,2-diamino-4-nitrobenzene;
1-amino-2-β-hydroxyethylamino-5-nitrobenzene;
1,2-bis(β-hydroxyethylamino)-4-n itrobenzene;
1-amino-2-[tris(hydroxymethyl)methylamino]-5-nitrobenzene;
1-hydroxy-2-amino-5-nitrobenzene;
1-hydroxy-2-amino-4-nitrobenzene;
1-hydroxy-3-nitro-4-aminobenzene;
1-hydroxy-2-amino-4,6-dinitrobenzene;
1-β-hydroxyethyloxy-2-β-hydroxyethylamino-5-nitrobenzene;
1-methoxy-2-β-hydroxyethylamino-5-nitrobenzene;
1-β-hydroxyethyloxy-3-methylamino-4-nitrobenzene;
1-β,γ-dihydroxypropyloxy-3-methylamino-4-nitrobenzene;
1-β-hydroxyethylamino-4-β,γ-dihydroxypropyloxy-2-nitrobenzene;
1-β,γ-dihydroxypropylamino-4-trifluoromethyl-2-nitrobenzene;
1-β-hydroxyethylamino-4-trifluoromethyl-2-nitrobenzene;
1-β-hydroxyethylamino-3-methyl-2-nitrobenzene;
1-β-aminoethylamino-5-methoxy-2-nitrobenzene;
1-hydroxy-2-chloro-6-ethylamino-4-nitrobenzene;
1-hydroxy-2-chloro-6-amino-4-nitrobenzene;
1-hydroxy-6-[bis(β-hydroxyethyl)amino]-3-nitrobenzene;
1-β-hydroxyethylamino-2-nitrobenzene;
1-hydroxy-4-β-hydroxyethylamino-3-nitrobenzene.

Non-limiting examples of the aforementioned azo direct dyes that may be used according to the present disclosure include, but are not limited to the cationic azo dyes described in patent applications WO 95/15144, WO 95/01772 and EP 714 954. The disclosures related to these azo direct dyes are herein incorporated by reference. Of these dyes, non-limiting mention is made of following compounds:

1,3-dimethyl-2-[[4-(dimethylamino)phenyl]azo]-1H-imidazolium chloride;
1,3-dimethyl-2-[(4-aminophenyl)azo]-1H-imidazolium chloride; and
1-methyl-4-[(methylphenylhydrazono)methyl]pyridinium methyl sulfate.

Further non-limiting examples of azo direct dyes include the following dyes described in the Color Index International 3rd edition:

Disperse Red 17;
Acid Yellow 9;
Acid Black 1;
Basic Red 22;
Basic Red 76;
Basic Yellow 57;
Basic Brown 16;
Acid Yellow 36;
Acid Orange 7;
Acid Red 33;
Acid Red 35;
Basic Brown 17;
Acid Yellow 23;
Acid Orange 24; and
Disperse Black 9.

Non-limiting mention is also made of 1-(4'-aminodiphenylazo)-2-methyl-4-[bis(β-hydroxyethyl)amino]benzene and 4-hydroxy-3-(2-methoxyphenylazo)-1-naphthalenesulfonic acid.

Examples of the aforementioned quinone direct dyes include, but are not limited to the following dyes:

Disperse Red 15;
Solvent Violet 13;
Acid Violet 43;
Disperse Violet 1;
Disperse Violet 4;
Disperse Blue 1;
Disperse Violet 8;
Disperse Blue 3;
Disperse Red 11;
Acid Blue 62;
Disperse Blue 7;
Basic Blue 22;
Disperse Violet 15; and
Basic Blue 99;

as well as the following compounds:
1-N-methylmorpholiniumpropylamino-4-hydroxyanthraquinone;
1-aminopropylamino-4-methylaminoanthraquinone;
1-aminopropylaminoanthraquinone;
5-β-hydroxyethyl-1,4-diaminoanthraquinone;
2-aminoethylaminoanthraquinone; and
1,4-bis(β,γ-dihydroxypropylamino)anthraquinone.

Examples of the aforementioned azine dyes include, but are not limited to the following compounds:

Basic Blue 17; and
Basic Red 2.

Non-limiting examples of the aforementioned triarylmethane dyes include the following compounds:

Basic Green 1;
Acid Blue 9;
Basic Violet 3;
Basic Violet 14;
Basic Blue 7;
Acid Violet 49;
Basic Blue 26; and
Acid Blue 7.

Non-limiting examples of the aforementioned indoamine dyes include the following compounds:

2-β-hydroxyethylamino-5-[bis(β-4'-hydroxyethyl)-amino]-anilino-1,4-benzoquinone;
2-β-hydroxyethylamino-5-(2'-methoxy-4'-amino)anilino-1,4-benzoquinone;
3-N-(2'-chloro-4'-hydroxy)phenylacetylamino-6-methoxy-1,4-benzoquinoneimine;
3-N-(3'-chloro-4'-methylamino)phenylureido-6-methyl-1,4-benzoquinoneimine; and
3-[4'-N-(ethylcarbamylmethyl)amino]phenylureido-6-methyl-1,4-benzoquinoneimine.

Examples of the aforementioned natural direct dyes that may be used according to the disclosure include, but are not limited to lawsone, juglone, alizarin, purpurin, carminic acid, kermesic acid, purpurogallin, protocatechaldehyde, indigo, isatin, curcumin, spinulosin and apigenidin. Extracts or decoctions containing these natural dyes may also be used, including henna-based poultices or extracts.

The additional direct dye(s) may be present in the dye composition in an amounts ranging from 0.001% to 20% by weight, such as from 0.01 to 10% by weight, relative to the total weight of the dye composition.

In a non-limiting embodiment the oxidation bases that may be present in the dye compositions of the present disclosure are chosen from phenylenediamines, bis(phenyl) alkylenediamines, para-aminophenols, ortho-aminophenols and heterocyclic bases other than the heterocyclic para-phenylenediamines of formula (I), and the addition salts thereof.

Non-limiting examples of the aforementioned para-phenylenediamines include para-phenylenediamine, para-tolylenediamine, 2-chloro-para-phenylenediamine, 2,3-dimethyl-para-phenylenediamine, 2,6-dimethyl-para-phenylenediamine, 2,6-diethyl-para-phenylenediamine, 2,5-dimethyl-para-phenylenediamine, N,N-dimethyl-para-phenylenediamine, N,N-diethyl-para-phenylenediamine, N,N-dipropyl-para-phenylenediamine, 4-amino-N,N-diethyl-3-methylaniline, N,N-bis(β-hydroxyethyl)-para-phenylenediamine, 4-N,N-bis(β-hydroxyethyl)amino-2-methylaniline, 4-N,N-bis(β-hydroxyethyl)amino-2-chloroaniline, 2-β-hydroxyethyl-para-phenylenediamine, 2-fluoro-para-phenylenediamine, 2-isopropyl-para-phenylenediamine, N-(β-hydroxypropyl)-para-phenylenediamine, 2-hydroxymethyl-para-phenylenediamine, N,N-dimethyl-3-methyl-para-phenylenediamine, N-ethyl-N-(β-hydroxyethyl)-para-phenylenediamine, N-(β,γ-dihydroxypropyl)-para-phenylenediamine, N-(4'-aminophenyl)-para-phenylenediamine, N-phenyl-para-phenylenediamine, 2-β-hydroxyethyloxy-para-phenylenediamine, 2-β-acetylaminoethyloxy-para-phenylenediamine, N-(β-methoxyethyl)-para-phenylenediamine, 4-aminophenylpyrrolidine, 2-thienyl-para-phenylenediamine, 2-β-hydroxyethylamino-5-aminotoluene, 3-hydroxy-1-(4'-aminophenyl)pyrrolidine, and the acid addition salts thereof.

In a non-limiting embodiment, the para-phenylenediamine above is chosen from para-phenylenediamine, para-tolylenediamine, 2-isopropyl-para-phenylenediamine, 2-β-hydroxyethyl-para-phenylenediamine, 2-β-hydroxyethyloxy-para-phenylenediamine, 2,6-dimethyl-para-phenylenediamine, 2,6-diethyl-para-phenylenediamine, 2,3-dimethyl-para-phenylenediamine, N,N-bis(β-hydroxyethyl)-para-phenylenediamine, 2-chloro-para-phenylenediamine and 2-β-acetylaminoethyloxy-para-phenylenediamine, and the acid addition salts thereof.

Non-limiting examples of the aforementioned bis(phenyl) alkylenediamines include N,N'-bis(β-hydroxyethyl)-N,N'-bis(4'-aminophenyl)-1,3-diaminopropanol; N,N'-bis(β-hydroxyethyl)-N,N'-bis(4'-aminophenyl)ethylenediamine; N,N'-bis(4-aminophenyl)tetra-methylenediamine; N,N'-bis(β-hydroxyethyl)-N,N'-bis(4-aminophenyl)tetramethylenediamine; N,N'-bis(4-methylaminophenyl)tetramethylenediamine; N,N'-bis(ethyl)-N,N'-bis(4'-amino-3'-methylphenyl) ethylenediamine; 1,8-bis(2,5-diaminophenoxy)-3,6-dioxaoctane; and the addition salts thereof.

Examples of the aforementioned para-aminophenols include, but are not limited to para-aminophenol, 4-amino-3-methylphenol, 4-amino-3-fluorophenol, 4-amino-3-chlorophenol, 4-amino-3-hydroxymethylphenol, 4-amino-2-methylphenol, 4-amino-2-hydroxymethylphenol, 4-amino-2-methoxymethylphenol, 4-amino-2-aminomethylphenol, 4-amino-2-(β-hydroxyethylaminomethyl)phenol, 4-amino-2-fluorophenol, and the acid addition salts thereof.

Non-limiting examples of the aforementioned ortho-aminophenols include 2-aminophenol, 2-amino-5-methylphenol, 2-amino-6-methylphenol, 5-acetamido-2-aminophenol, and the addition salts thereof.

Non-limiting examples of the aforementioned heterocyclic bases include pyridine derivatives, pyrimidine derivatives and pyrazole derivatives.

Examples of the aforementioned pyridine derivatives include, but are not limited to the compounds described, for example, in patents GB 1 026 978 and GB 1 153 196, such as 2,5-diaminopyridine, 2-(4-methoxyphenyl)amino-3-aminopyridine, 3,4-diaminopyridine, and the addition salts thereof.

Other non-limiting examples of pyridine oxidation bases that may be used include 3-aminopyrazolo[1,5-a]pyridine oxidation bases or addition salts thereof described, for example, in patent application FR 2 801 308, such as pyrazolo[1,5-a]pyrid-3-ylamine, 2-acetylaminopyrazolo[1,5-a]pyrid-3-ylamine, 2-morpholin-4-ylpyrazolo[1,5-a]pyrid-3-ylamine, 3-aminopyrazolo[1,5-a]pyridine-2-carboxylic acid, 2-methoxypyrazolo[1,5-a]pyrid-3-ylamino, (3-aminopyrazolo[1,5-a]pyrid-7-yl) methanol, 2-(3-aminopyrazolo[1,5-a]pyrid-5-yl)ethanol, 2-(3-aminopyrazolo[1,5-a]pyrid-7-yl)ethanol, (3-aminopyrazolo[1,5-a]pyrid-2-yl)methanol, 3,6-diaminopyrazolo[1,5-a]pyridine, 3,4-diaminopyrazolo[1,5-a]pyridine, pyrazolo[1,5-a]pyridine-3,7-diamine, 7-morpholin-4-ylpyrazolo[1,5-a]pyrid-3-ylamine, pyrazolo[1,5-a]pyridine-3,5-diamine, 5-morpholin-4-ylpyrazolo[1,5-a]pyrid-3-ylamine, 2-[(3-aminopyrazolo[11,5-a]pyrid-5-yl)(2-hydroxyethyl)amino] ethanol, 2-[(3-aminopyrazolo[1,5-a]pyrid-7-yl)(2-hydroxyethyl)amino]ethanol, 3-aminopyrazolo[1,5-a]pyridin-5-ol, 3-amino-pyrazolo[1,5-a]pyridin-4-ol, 3-aminopyrazolo[1,5-a]pyridin-6-ol, 3-aminopyrazolo[1,5-a]pyridin-7-ol, and the addition salts thereof.

Non-limiting examples of the aforementioned pyrimidine derivatives include the compounds described in patents DE 2 359 399; EP 0 770 375, and patent applications JP 88-169 571; JP 05-63124; and WO 96/15765, such as 2,4,5,6-tetraminopyrimidine, 4-hydroxy-2,5,6-triaminopyrimidine, 2-hydroxy-4,5,6-triaminopyrimidine, 2,4-dihydroxy-5,6-diaminopyrimidine, 2,5,6-triaminopyrimidine, the addition salts thereof, and the tautomeric forms thereof, when a tautomeric equilibrium exists.

Non-limiting examples of the aforementioned pyrazole derivatives include the compounds described in patents DE 3 843 892 and DE 4 133 957, and patent applications WO 94/08969, WO 94/08970, FR-A-2 733 749 and DE 195 43 988, such as 4,5-diamino-1-methylpyrazole, 4,5-diamino-1-(β-hydroxyethyl)pyrazole, 3,4-diaminopyrazole, 4,5-diamino-1-(4'-chlorobenzyl)pyrazole, 4,5-diamino-1,3-dimethylpyrazole, 4,5-diamino-3-methyl-1-phenylpyrazole, 4,5-diamino-1-methyl-3-phenylpyrazole, 4-amino-1,3-dimethyl-5-hydrazinopyrazole, 1-benzyl-4,5-diamino-3-methylpyrazole, 4,5-diamino-3-tert-butyl-1-methylpyrazole, 4,5-diamino-1-tert-butyl-3-methylpyrazole, 4,5-diamino-1-(β-hydroxyethyl)-3-methylpyrazole, 4,5-diamino-1-ethyl-3-methylpyrazole, 4,5-diamino-1-ethyl-3-(4'-methoxyphenyl) pyrazole, 4,5-diamino-1-ethyl-3-hydroxymethylpyrazole, 4,5-diamino-3-hydroxymethyl-1-methylpyrazole, 4,5-diamino-3-hydroxymethyl-1-isopropylpyrazole, 4,5-diamino-3-methyl-1-isopropylpyrazole, 4-amino-5-(2'-aminoethyl) amino-1,3-dimethylpyrazole, 3,4,5-triaminopyrazole, 1-methyl-3,4,5-triaminopyrazole, 3,5-diamino-1-methyl-4-methylaminopyrazole, 3,5-diamino-4-(β-hydroxyethyl) amino-1-methylpyrazole, and the addition salts thereof. 4,5-Diamino-1-(β-triethoxyethyl)pyrazole may also be used.

The oxidation bases disclosed herein may be present in an amount ranging from approximately 0.001% to 20% by weight, such as from 0.005% to 6% by weight, relative to the total weight of the dye composition.

The dye composition of the present disclosure may further comprise one or more oxidation dye precursors chosen from couplers, including those conventionally used for dyeing keratin fibers, such as meta-phenylenediamines, meta-diphenols, naphthalene-based couplers, heterocyclic couplers, and the addition salts thereof.

Non-limiting examples of the aforementioned couplers include 1,3-dihydroxy-benzene, 1,3-dihydroxy-2-methylbenzene, 4-chloro-1,3-dihydroxybenzene, 2,4-diamino-1-(β-hydroxyethyloxy)benzene, 2-amino-4-(β-hydroxyethylamino)-1-methoxybenzene, 1,3-diaminobenzene, 1,3-bis(2,4-diaminophenoxy)propane, 3-ureidoaniline, 3-ureido-1-dimethylaminobenzene, sesamol, 1-β-hydroxyethylamino-3,4-methylenedioxybenzene, x-naphthol, 2-methyl-1-naphthol, 6-hydroxyindole, 4-hydroxyindole, 4-hydroxy-N-methylindole, 2-amino-3-hydroxypyridine, 6-hydroxybenzomorpholine, 3,5-diamino-2,6-dimethoxypyridine, 1-N-(β-hydroxyethyl)amino-3,4-methylenedioxybenzene, 2,6-bis(β-hydroxyethylamino)toluene, and the addition salts thereof.

In the composition of the present disclosure, the couplers are generally present in an amount ranging from 0.001% to 20% by weight, such as from 0.01% to 6% by weight, relative to the total weight of the dye composition.

In one embodiment, the addition salts of the oxidation bases and couplers that may be used in the context of the disclosure are chosen from acid addition salts, including, but not limited to the hydrochlorides, hydrobromides, sulfates, citrates, succinates, tartrates, lactates, tosylates, benzenesulfonates, phosphates and acetates; and basic addition salts, including, but not limited to, sodium hydroxide, potassium hydroxide, ammonia, amines and alkanolamines.

The medium that is suitable for dyeing, also known as the dye support, is a cosmetic medium generally comprising water or a mixture of water and one or more organic solvents to dissolve the compounds that are not sufficiently water-soluble. Non-limiting examples of organic solvents include $C_1$-$C_4$ lower alkanols, such as ethanol and isopropanol; polyols and polyol ethers, such as 2-butoxyethanol, propylene glycol, propylene glycol monomethyl ether, diethylene glycol monoethyl ether and monomethyl ether; aromatic alcohols, such instance benzyl alcohol or phenoxyethanol; and mixtures thereof.

The above solvents are generally present in the dye composition in an amount ranging from 1% to 40% by weight, such as 5% to 30 by weight, relative to the total weight of the dye composition.

The dye composition in accordance with the disclosure may further comprise various adjuvants conventionally used in hair dye compositions. Non-limiting examples of such adjuvants include anionic, cationic, nonionic, amphoteric or zwitterionic surfactants or mixtures thereof; anionic, cationic, nonionic, amphoteric or zwitterionic polymers or mixtures thereof; mineral or organic thickeners, such as anionic, cationic, nonionic and amphoteric associative thickeners; antioxidants; penetrating agents; sequestering agents; fragrances; buffers; dispersants; conditioners, such as volatile or non-volatile, modified or unmodified silicones; film-forming agents; ceramides; preserving agents; and opacifiers.

The above adjuvants are generally present in the dye composition in an amount ranging from 0.01% to 20% by weight relative to the weight of the composition.

Needless to say, a person skilled in the art will take care to select the aforementioned optional components such that the advantageous properties intrinsically associated with the oxidation dye composition are not substantially adversely affected.

The pH of the dye composition in accordance with the disclosure generally ranges from 3 to 12, such as from 5 to 11. The pH may be adjusted to the desired value via the addition of acidifying or basifying agents conventionally used in compositions for dyeing keratin fibers. Alternatively, pH may be controlled through the use of standard buffer systems.

Non-limiting examples of the aforementioned acidifying agents include mineral or organic acids, such as hydrochloric acid, orthophosphoric acid, or sulfuric acid; carboxylic acids, such as acetic acid, tartaric acid, citric acid or lactic acid; and sulfonic acids.

Non-limiting examples of the aforementioned basifying agents include aqueous ammonia; alkaline carbonates; alkanolamines such as monoethanolamine; diethanolamine; triethanolamine and derivatives thereof; sodium hydroxide; potassium hydroxide; and the compounds of formula (II) below:

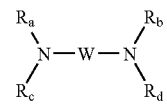

(II)

wherein:

W is a propylene residue that is optionally substituted with a hydroxyl group or a $C_1$-$C_4$ alkyl radical;

$R_a$, $R_b$, $R_c$ and $R_d$ may be identical or different, and represent a hydrogen atom, a $C_1$-$C_4$ alkyl, or a $C_1$-$C_4$ hydroxyalkyl radical.

The dye composition according to the disclosure may be in various forms, such as in the form of liquids, creams or gels, or in any other form that is suitable for dyeing keratin fibers such as human hair.

The process for dyeing keratin fiber according to the present disclosure comprises the application of a dye composition according to the present disclosure to keratin fibers, followed by leaving the composition on the fibers for a time sufficient to allow the coloration of the hair. This time period is generally from 5 minutes to 1 hour, such as from 15 minutes to 1 hour.

The process for dyeing keratin fibers may further comprise the use of an oxidizing agent at acidic, neutral or alkaline pH. The oxidizing agent may be added to the disclosed composition at the time of use, or may be used a component of an oxidizing composition, wherein the oxidizing composition is applied simultaneously or sequentially to the dye composition disclosed herein.

In a non-limiting embodiment of the process of the present disclosure, the composition comprising the compound(s) of formula A-L-B comprises at least one oxidation dye precursor.

In another non-limiting embodiment of the process of the present disclosure, the composition comprising the compound of formula A-L-B and optionally at least one oxidation dye precursor is mixed, such as at the time of use, with a composition containing, in a medium that is suitable for dyeing, at least one oxidizing agent. The mixture obtained is then applied to the keratin fibers. The mixture is left on the keratin fibers for a time period from 5 to 60 minutes, i.e. 15 to 60 minutes, after which the keratin fibers are rinsed, washed with shampoo, rinsed again, and then dried.

Non-limiting examples of oxidizing agents conventionally used for the oxidation dyeing of keratin fibers include hydrogen peroxide, urea peroxide, alkali metal bromates, persalts such as perborates and persulfates, peracids, oxidase enzymes such as peroxidases, 2-electron oxidoreductases such as uricases, and 4-electron oxygenases such as laccases. In a non-limiting embodiment, hydrogen peroxide is used as the oxidizing agent.

The oxidizing composition may further comprise various adjuvants conventionally used in hair dye compositions and as defined above.

In a non-limiting embodiment, the pH of the oxidizing composition containing the oxidizing agent is such that, after mixing with the dye composition, the pH of the resulting composition applied to the keratin fibers ranges from 3 to 12, such as from 5 to 11 or from 6 to 8.5. The pH may be adjusted to the desired value by means of acidifying or basifying pH regulators conventionally used in the dyeing of keratin fibers and as defined above.

The composition applied to the keratin fibers may be in various forms, such as in the form of liquids, creams or gels, or in any other form that is suitable for dyeing keratin fibers, and especially human hair. In particular, it may be packaged under pressure in an aerosol can in the presence of a propellant and may form a mousse.

Another aspect of the present disclosure is a multi-compartment device or dyeing "kit", comprising a first compartment containing the dye composition defined above and a second compartment containing an oxidizing agent. This device may be equipped with an applicator for applying the desired mixture to the hair. Non-limiting examples of such devices include those devices described in patent FR 2 586 913.

With this device, keratin fibers may be dyed using a process that involves mixing a dye composition of the disclosure with an oxidizing agent as defined above, and applying the mixture to the keratin fibers for a time that is sufficient to develop a desired coloration.

Other than in the operating examples, or where otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present invention. At the very least, and not as an attempt to limit the application of the doctrine of equivalents to the scope of the claims, each numerical parameter should be construed in light of the number of significant digits and ordinary rounding approaches.

Notwithstanding that the numerical ranges and parameters setting forth the broad scope of the invention are approximations, the numerical values set forth in the specific example are reported as precisely as possible. Any numerical value, however, inherently contains certain errors necessarily resulting from the standard deviation found in their respective testing measurements.

The following examples are intended to illustrate the invention in a non-limiting manner.

EXAMPLES OF DYE PREPARATIONS

The claimed products were produced via a sequence of reactions known to those skilled in the art.

Example 1

Synthesis of 4-{4-[(E)(1,3-dimethyl-1H-imidazol-3-ium-2-yl)diazenyl]phenyl}-1-[6-(4-{4-[(E)(1,3-dimethyl-1H-imidazol-3-ium-2-yl)diazenyl]phenyl}-1-methylpiperazin-1-ium-1-yl)hexyl]-1-methylpiperazin-1-ium dichloride bis(methyl sulfate) (II)

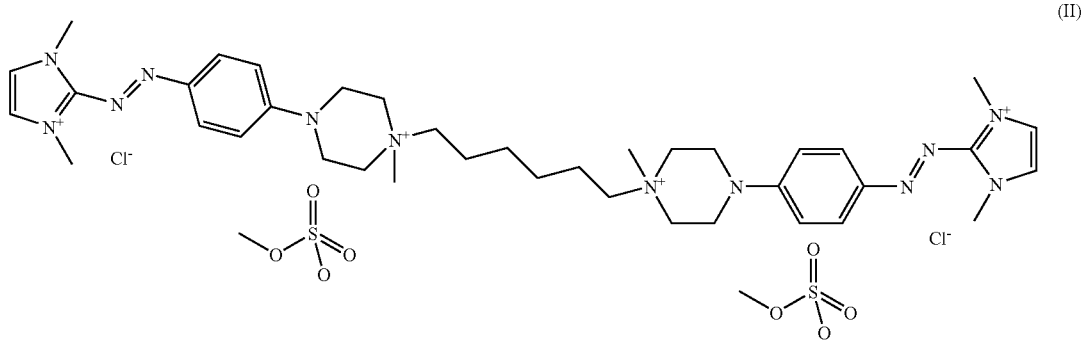

Step 1

2-[(E)(4-{4-[6-(4-{4-[(E)(1,3-dimethyl-1H-imidazol-3-ium-2-yl)diazenyl]phenyl}piperazin-1-yl)hexyl]piperazin-1-yl}phenyl)diazenyl]-1,3-dimethyl-1H-imidazol-3-ium chloride (I) was synthesized by dissolving 1,3-Dimethyl-2-[(E)(4-piperazin-1-ylphenyl)diazenyl]-1H-imidazol-3-ium chloride (0.9 g) in DMF (20 ml), Br(CH$_2$)$_6$Br (0.5 mol

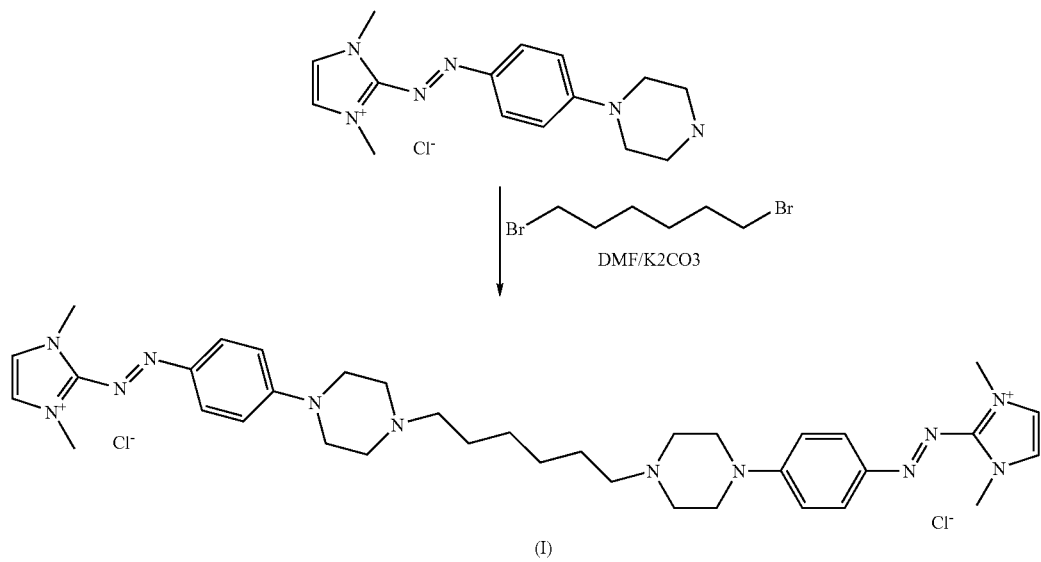

eq.), and potassium carbonate (1 mol. eq.). The reaction mixture was stirred at 80° C. for 24 hours and then cooled to room temperature and filtered. The crude product was precipitated from diisopropyl ether (200 ml) and purified by chromatography.

The reaction was monitored by thin-layer chromatography (TLC) in the normal phase with a silica adsorbent and an eluent mixture of $CH_2Cl_2$, ethanol, and a pH 9 buffer (1/8/1).

Step 2

2-[(E)(4-{4-[6-(4-{4-[(E)(1,3-Dimethyl-1H-imidazol-3-ium-2-yl)diazenyl]phenyl}piperazin-1-yl)hexyl]piperazin-1-yl}phenyl)diazenyl]-1,3-dimethyl-1H-imidazol-3-ium chloride (I, 0.3 g) was dissolved in DMF (20 ml) and dimethyl sulfate (2.2 mol eq.) and stirred at 80° C. for 6 hours. The crude product was precipitated from diisopropyl ether (200 ml) and purified by chromatography.

The reaction was monitored by TLC in the normal phase, using a silica adsorbent and an eluent mixture of $CH_2Cl_2$, ethanol, and a pH 9 buffer (1/8/1).

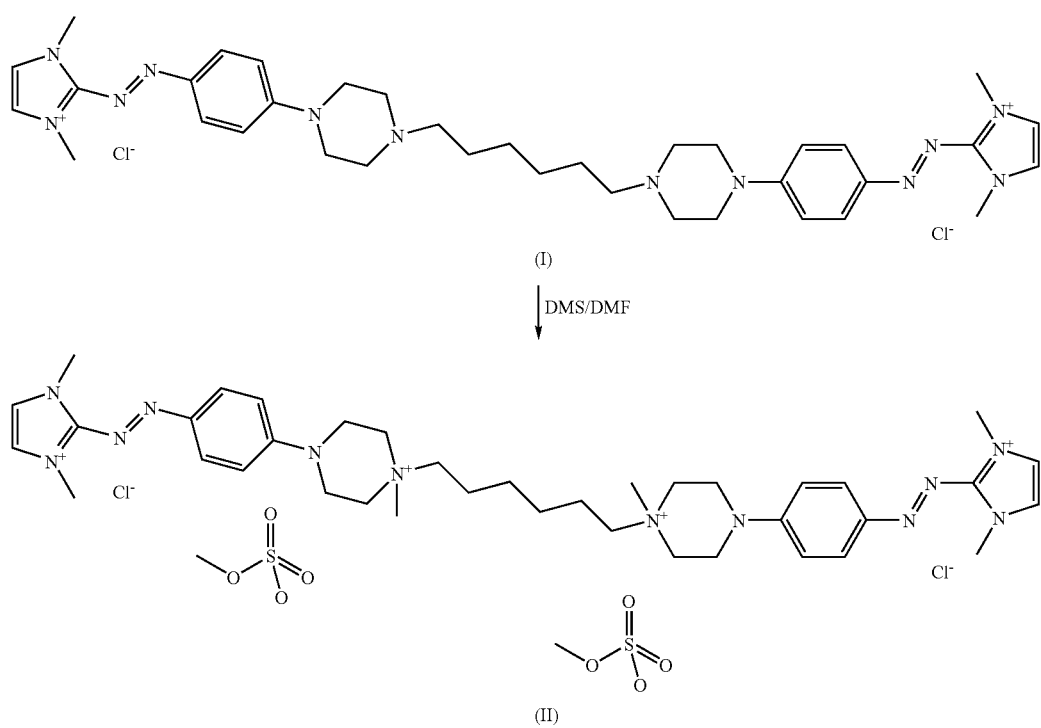

Example 2

Synthesis of 2-{(E)[4-({3-[3-(6-{1-[3-({4-[(E)(1,3-dimethyl-1H-imidazol-3-ium-2-yl)diazenyl]phenyl}amino)propyl]-1H-imidazol-3-ium-3-yl}hexyl)-1H-imidazol-3-ium-1-yl]propyl}amino)phenyl]diazenyl}-1,3-dimethyl-1H-imidazol-3-ium tetrachloride (III)

2-[(E)(4-{[3-(1H-Imidazol-1-yl)propyl]amino}phenyl)diazenyl]-1,3-dimethyl-1H-imidazol-3-ium chloride (1 g) was dissolved in DMF (20 ml) and Br(CH$_2$)$_6$Br (0.5 mol eq.). The reaction mixture was stirred at 80° C. for 24 hours and then cooled to room temperature. The crude product was precipitated from diisopropyl ether (200 ml) and purified by chromatography. The final step was a standard ion exchange on resin activated with hydrochloric acid.

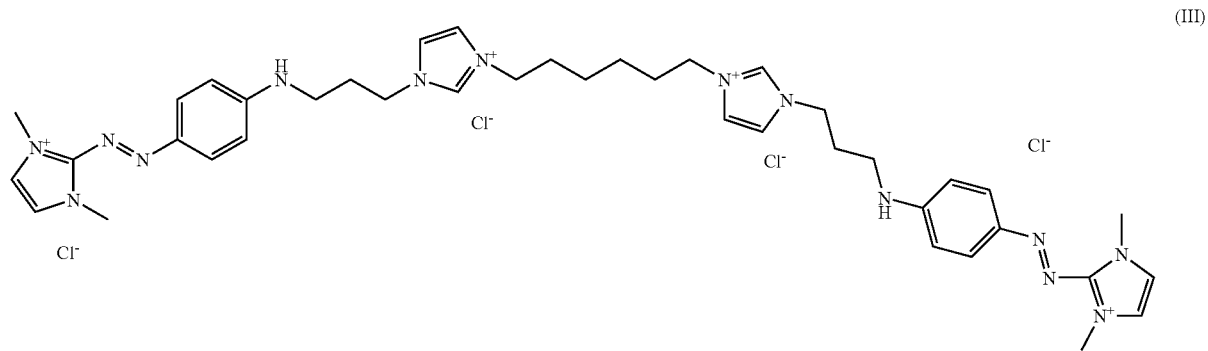

(III)

Step 2

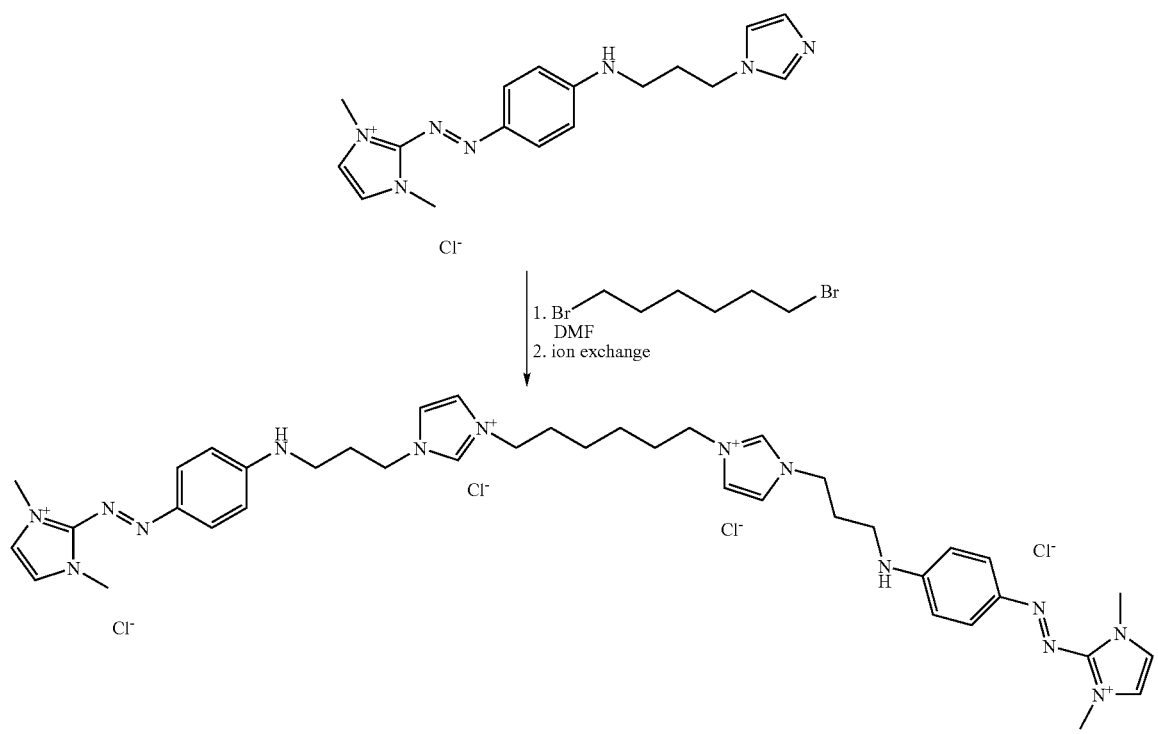

The reaction was monitored by TLC in the normal phase, using a silica adsorbent and an eluent mixture of CH$_2$Cl$_2$, ethanol, and a pH 9 buffer (1/8/1).

EXAMPLES OF DYE COMPOSITIONS

|  | A | B |
|---|---|---|
| Dye of formula (II) | 0.1 g | — |
| Dye of formula (III) | — | 0.1 g |
| Alkyl(C8-C10)polyglucoside (percentage of active material) | 3 | 3 |
| Ethanol | 10 g | 10 g |
| 2-Amino-2-methyl-1-propanol | qs pH 8.5 | qs pH 8.5 |
| Water | qs 100 g | qs 100 g |

Each of the compositions A and B is applied to the hair for 30 minutes. After rinsing and drying, the hair is dyed in a sparingly selective, strong red shade.

Example 3

Synthesis of the dichloride methosulfate salt of 2-{(E)[4-({3-[[3-({4-[(E)(1,3-dimethyl-1H-imidazol-3-ium-2-yl)diazenyl]-phenyl}amino)propyl](dimethyl)ammonio]propyl}amino)phenyl]diazenyl}-1,3-dimethyl-1H-imidazol-3-ium (IV)

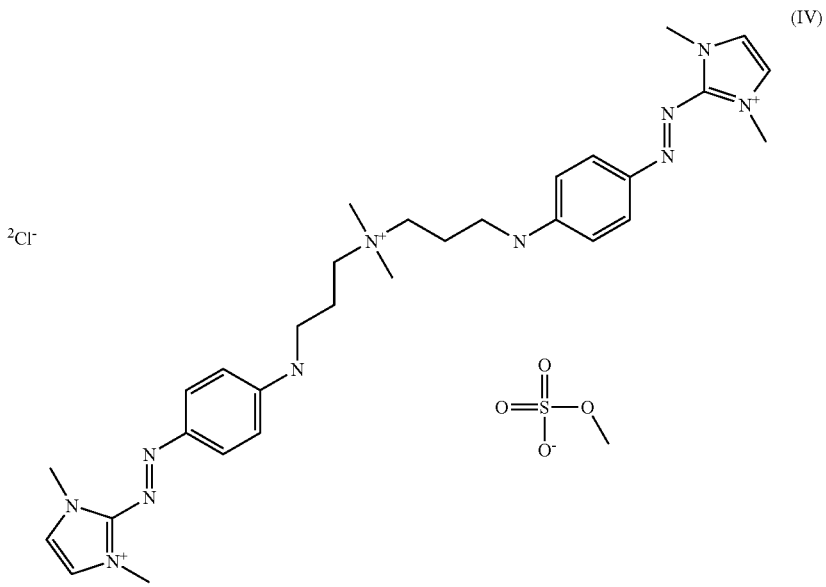

Step 1:

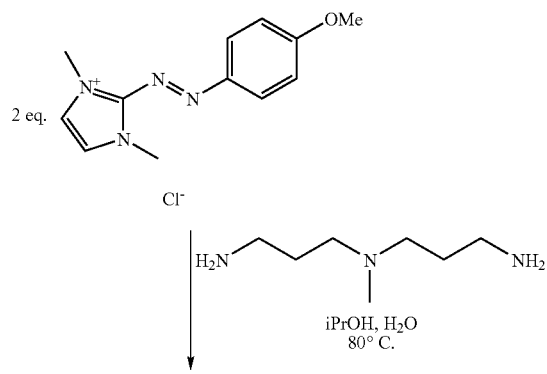

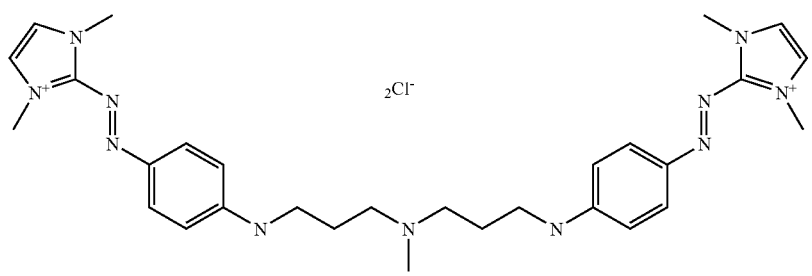

2-[(E)(4-Methoxyphenyl)diazenyl]-1,3-dimethyl-1H-imidazol-3-ium chloride (10 g, 0.0375 mol) was dissolved in isopropanol (30 ml) and water (20 ml). 2.72 g (0.0187 mol) of N,N-bis(3-aminopropyl)-N-methylamine was then added to the reaction medium. This medium was stirred at 80° C. for 12 hours and then cooled to room temperature. The crude product precipitated from the isopropanol. The crude product was recrystallized several times from ethanol. The precipitate obtained was filtered off and then dried under vacuum.

The reaction was monitored by TLC in the normal phase, using a silica adsorbent and an eluent mixture of $CH_2Cl_2$, ethanol, and a pH 9 buffer (1/8/1). The analyses were in accordance with the expected product.

Step 2:

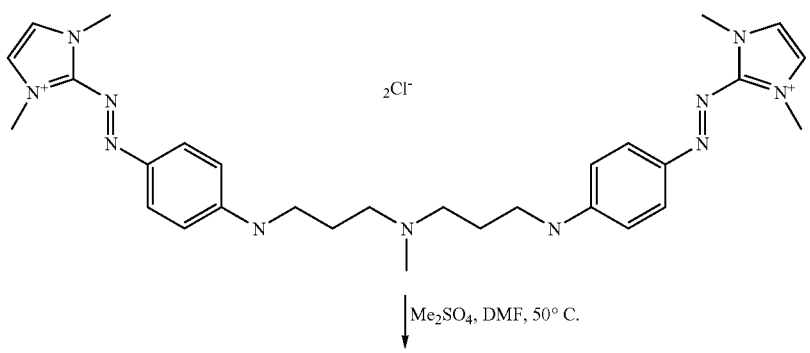

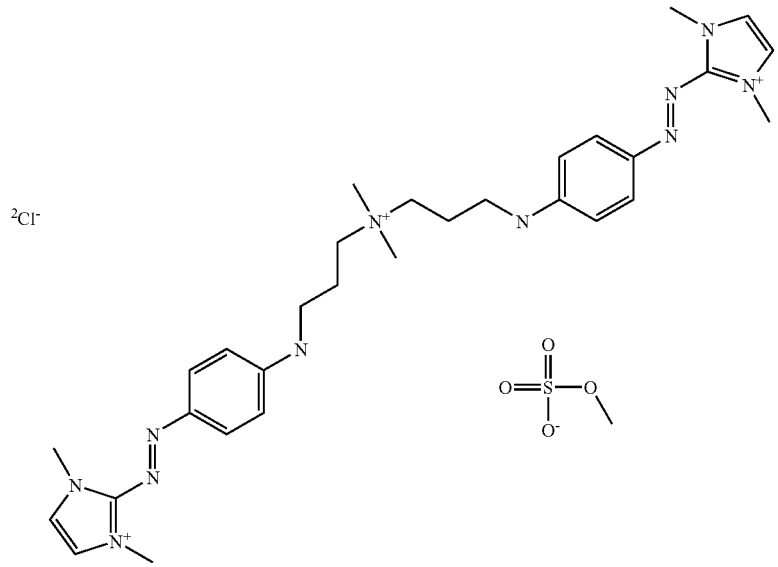

2-{(E)[4-({3-[[3-({4-[(E) (1,3-Dimethyl-1H-imidazol-3-ium-2-yl)diazenyl]phenyl}amino)propyl](methyl)amino]propyl}amino)phenyl]diazenyl}-1,3-dimethyl-1H-imidazol-3-ium dichloride (1.5 g) was dissolved in dimethylformamide (23 ml). 0.38 ml of dimethyl sulfate was then added to the reaction medium. This medium was stirred at 50° C. for 22 hours and then cooled to room temperature. The expected crude product was precipitated from an ethyl acetate solution, filtered off and then dried under vacuum.

The reaction was monitored via TLC in the normal phase using a silica adsorbent and eluent mixture of BuOH, $H_2O$ and AcOH (40/30/15).

The analyses was in accordance with the expected product.

This dye was applied to hair, resulting in a sparingly selective, strong red shade.

What is claimed is:

1. A compound having the formula A-L-B, wherein A and B are chosen from arylazoimidazolium coloring functional groups, and L is a linker comprising at least one cationic group C.

2. The compound of claim 1, wherein the at least one cationic group C is chosen from aliphatic and heterocyclic cationic groups.

3. The compound of claim 2, wherein the heterocyclic cationic groups are chosen from imidazolium, piperidinium, pyridinium, pyrazolium and triazolium groups.

4. The compound of claim 3, wherein the heterocyclic cationic groups comprise an imidazolium group.

5. The compound of claim 2, wherein the aliphatic cationic groups are chosen from divalent radicals having the formula $-N^+-R_1R_2-$, where $R^1$ and $R_2$ are independently chosen from $C_1$-$C_{10}$ alkyl and $C_1$-$C_{10}$ mono- and polyhydroxyalkyl radicals.

6. The compound of claim 1, wherein the linker is chosen from linear and branched, saturated and unsaturated hydrocarbon based chains that are optionally terminated or interrupted by one or more carbonyl groups and/or one or more hetero atoms.

7. The compound of claim 1, wherein the linker comprises one or more aromatic rings or one or more aromatic or saturated heterocycles.

8. The compound of claim 6, wherein the hydrocarbon-based chains are substituted with at least one substituent chosen from hydroxyl, alkoxy, amino and alkylamino radicals, and halogens.

9. The compound of claim 6, wherein the linker L comprises a linear or branched $C_1$-$C_{40}$ hydrocarbon-based chain.

10. The compound of claim 9, wherein the linker L comprises a linear or branched $C_1$-$C_8$ hydrocarbon-based chain.

11. The compound of claim 1, wherein the compound of formula A-L-B is chosen from compounds of formula (I) below:

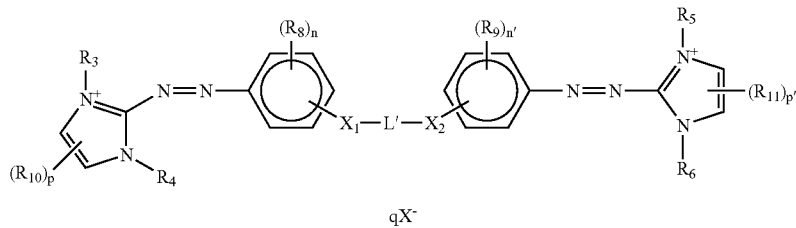

qX⁻ wherein:

- X₁ and X₂ are independently chosen from a piperazine ring substituted with at least one radical chosen from $C_1$-$C_8$ alkyl radicals; radicals —O— and —NR₇—, where R₇ is a hydrogen atom; $C_1$-$C_8$ alkyl radicals; and $C_1$-$C_8$ hydroxyalkyl radicals;
- R₃, R₄, R₅, and R₆ are independently chosen from $C_1$-$C_8$ alkyl radicals and $C_1$-$C_8$ hydroxyalkyl radicals;
- R₈ and R₉ are independently chosen from a hydrogen atom; $C_1$-$C_4$ alkyl radicals optionally substituted with one or more radicals chosen from hydroxyl, amino and $C_1$-$C_2$ (di)alkylamino radicals; carboxyl radicals; $C_1$-$C_2$ alkoxy radicals; amino radicals; $C_1$-$C_2$ (di)alkylamino radicals; and $C_2$-$C_4$ (poly)hydroxyalkylamino radicals;
- R₁₀ and R₁₁ are independently chosen from a hydrogen atom; linear and branched $C_1$-$C_4$ alkyl radicals optionally substituted with one or more radicals chosen from hydroxyl, $C_1$-$C_2$ alkoxy, $C_2$-$C_4$ (poly)hydroxyalkoxy, amino, $C_1$-$C_2$ (di)alkylamino, carboxyl and sulfonic radicals; optionally substituted phenyl radicals; carboxyl radicals; and sulfonylamino radicals;
- L' is a linker;
- the group X₁-L'-X₂ comprises at least one cationic group C;
- n and n' are integers ranging from 0 to 4;
- p and p' are integers ranging from 0 to 2;
- q is an integer ranging from 3 to 50; and
- X⁻ is an anion of mineral or organic origin.

12. The compound of claim 11, wherein q is an integer ranging from 3 to 5.

13. The compound of claim 12, wherein the value of q is chosen such that the compound of formula (I) is neutrally charged.

14. The compound of claim 12, where X⁻ is chosen from halide ions, sulfate or hydrogen sulfate ions, methosulfate ions, tosylate ions, carbonate ions, hydrogen carbonate ions, phosphate ions, nitrate ions, and citrate ions.

15. The compound of claim 1, wherein the compound of formula A-L-B is chosen from compounds having the following formulae:

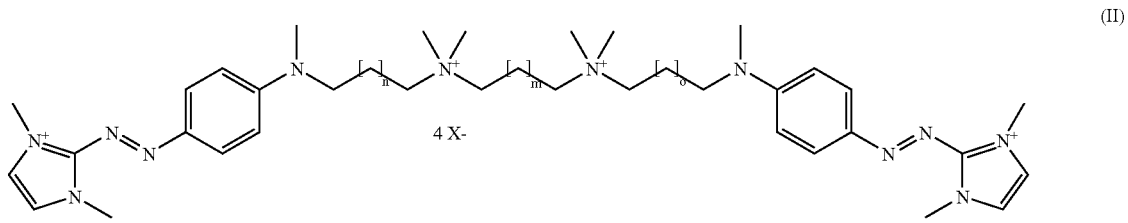

(II)

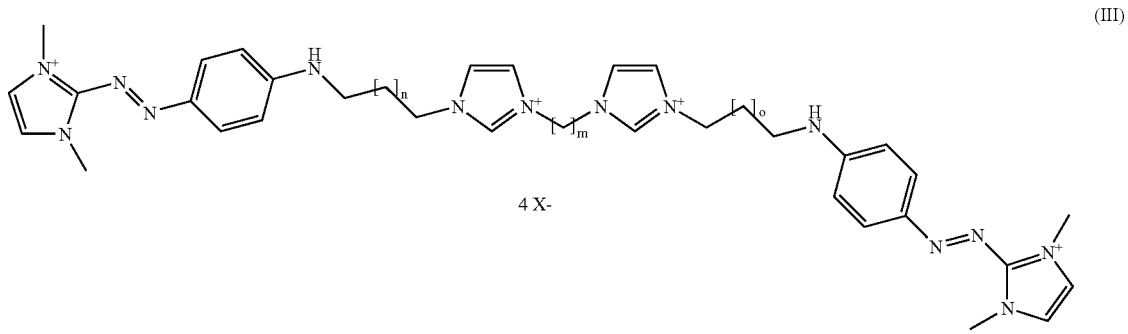

(III)

-continued

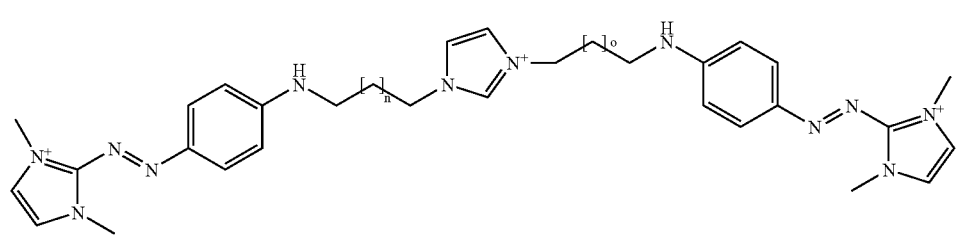
(IV)

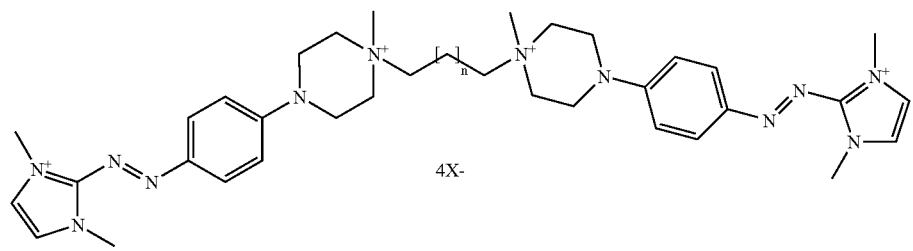
(V)

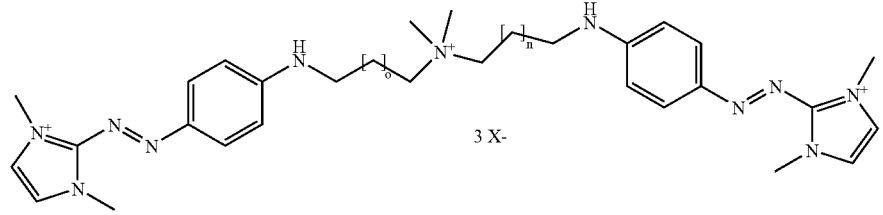
(VI)

wherein:

X⁻ is an anion of mineral or organic origin;

m and n are integers ranging from 0 to 20 and are chosen such that the linker contains from 1 to 40 carbon atoms.

16. The compound of claim 15, wherein m and n are integers ranging from 0 to 8.

17. The compound of claim 15, wherein m and n are chosen such that the linker contains from 1 to 8 carbon atoms.

18. A composition for dyeing keratin fibers comprising, in a medium suitable for dyeing, at least one direct dye, said direct dye comprising a compound of formula A-L-B, wherein A and B are chosen from arylazoimidazolium coloring functional groups, and L is a linker comprising at least one cationic group C, wherein said composition further comprises at least one oxidation base, and optionally at least one additional direct dye.

19. The composition of claim 18, wherein group C is chosen from aliphatic and heterocyclic cationic groups.

20. The composition of claim 19, wherein the heterocyclic cationic group is chosen from imidazolium, piperidinium, pyridinium, pyrazolium and triazolium groups.

21. The composition of claim 20, wherein the heterocyclic cationic group comprises an imidazolium group.

22. The composition of claim 19, wherein the aliphatic cationic group is chosen from divalent radicals having the formula —N⁺—R₁R₂—, where $R_1$ and $R_2$ are independently chosen from $C_1$-$C_{10}$ alkyl and $C_1$-$C_{10}$ mono- and polyhydroxyalkyl radicals.

23. The composition of claim 18, wherein the linker is chosen from linear and branched, saturated and unsaturated hydrocarbon based chains that are optionally terminated or interrupted by one or more carbonyl groups and/or one or more hetero atoms.

24. The composition of claim 18, wherein the linker comprises one or more aromatic rings or one or more aromatic or saturated heterocycles.

25. The composition of claim 23, wherein the hydrocarbon-based chains are substituted with a hydroxyl, alkoxy, amino or alkylamino radical, or a halogen.

26. The composition of claim 23, wherein the linker comprises a linear or branched $C_1$-$C_{40}$ carbon chain.

27. The composition of claim 26, wherein the linker comprises a linear or branched $C_1$-$C_8$ carbon chain.

28. The composition of claim 18, wherein the compound of formula A-L-B is chosen from compounds of formula (I) below:

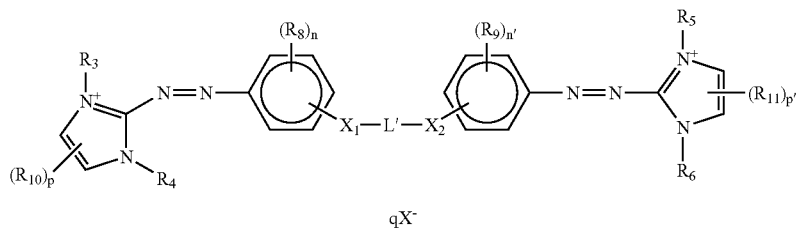

$qX^-$ wherein:

- $X_1$ and $X_2$ are independently chosen from a piperazine ring substituted with at least one radical chosen from $C_1$-$C_8$ alkyl radicals; radicals —O— and —$NR_7$—, where $R_7$ is a hydrogen atom; $C_1$-$C_8$ alkyl radicals; and a $C_1$-$C_8$ hydroxyalkyl radicals;
- $R_3$, $R_4$, $R_5$, and $R_6$ are independently chosen from $C_1$-$C_8$ alkyl radicals and $C_1$-$C_8$ hydroxyalkyl radicals;
- $R_8$ and $R_9$ are independently chosen from a hydrogen atom; $C_1$-$C_4$ alkyl radicals optionally substituted with one or more radicals chosen from hydroxyl, amino and $C_1$-$C_2$ (di)alkylamino radicals; carboxyl radicals; $C_1$-$C_2$ alkoxy radicals; amino radicals; $C_1$-$C_2$ (di)alkylamino radicals; and $C_2$-$C_4$ (poly)hydroxyalkylamino radicals;
- $R_{10}$ and $R_{11}$ are independently chosen from a hydrogen atom; linear and branched $C_1$-$C_4$-alkyl radicals optionally substituted with one or more radicals chosen from hydroxyl, $C_1$-$C_2$ alkoxy, $C_2$-$C_4$ (poly)hydroxyalkoxy, amino, $C_1$-$C_2$ (di)alkylamino, carboxyl and sulfonic radicals; optionally substituted phenyl radicals; carboxyl radicals; and sulfonylamino radicals;
- L' is a linker;
- the group $X_1$-L'-$X_2$ comprises at least one cationic group C;
- n and n' are integers ranging from 0 to 4;
- p and p' are integers ranging from 0 to 2;
- q is an integer ranging from 3 to 50; and
- $X^-$ is an anion of mineral or organic origin.

29. The dye composition of claim 28, wherein q is an integer ranging from 3 to 5.

30. The composition of claim 29, wherein value of q is chosen such that the compound of Formula (I) is neutrally charged.

31. The composition of claim 28, wherein $X^-$ is chosen from halide ions, sulfate or hydrogen sulfate ions, methosulfate ions, tosylate ions, carbonate ions, hydrogen carbonate ions, phosphate ions, nitrate ions, and citrate ions.

32. The composition of claim 18, wherein the compound of formula A-L-B is chosen from compounds having the following formulae:

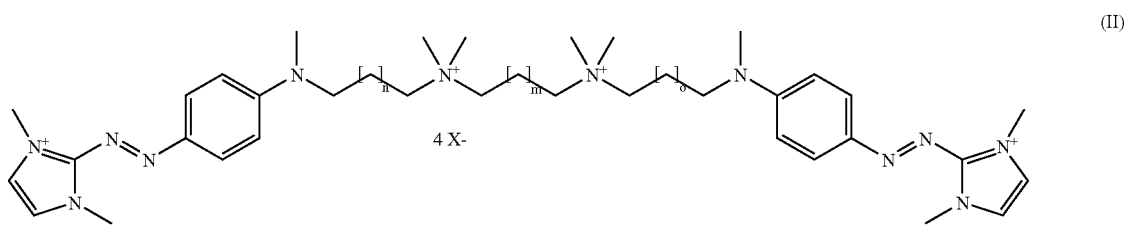

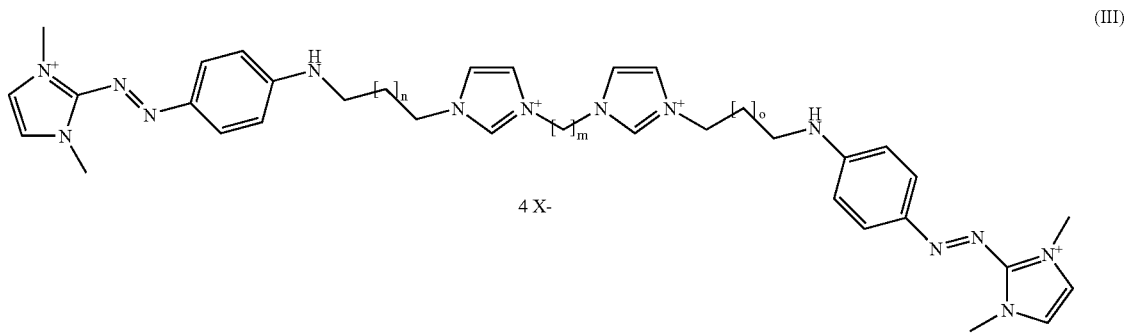

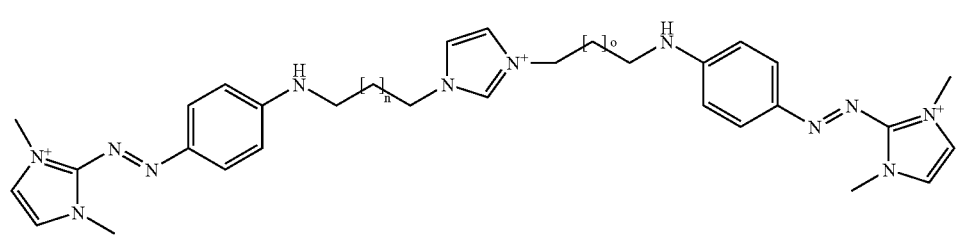

(IV)

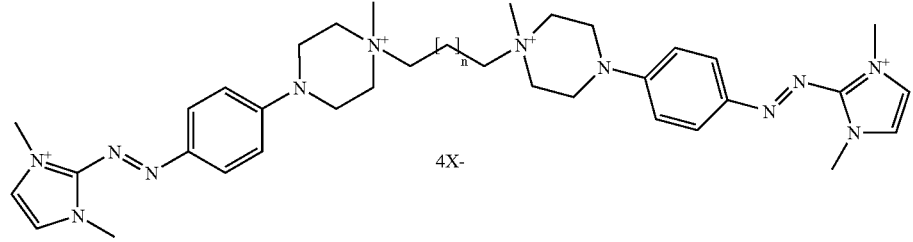

(V)

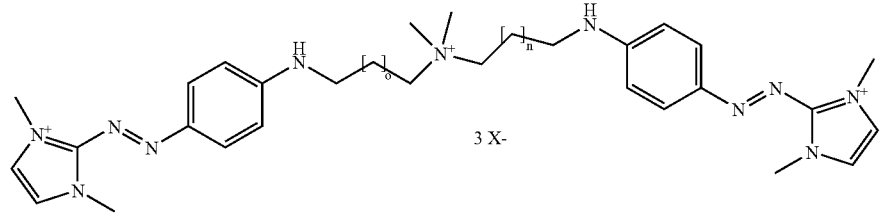

(VI)

wherein:

X⁻ is an anion of mineral or organic origin;

m and n are integers ranging from 0 to 20, and are chosen such that the linker contains from 1 to 40.

33. The composition of claim 32, wherein m and n are integers ranging from 0 to 8.

34. The composition of claim 32, wherein m and n are chosen such that the linker contains from 1 to 20 carbon atoms.

35. The composition of claim 32, wherein m and n are chosen such that he linker contains from 1 to 8 carbon atoms.

36. The composition of claim 18, wherein the composition comprises from 0.001% to 20% by weight of one or more direct dyes of the formula A-L-B, relative to the total weight of the composition.

37. The composition of claim 18, wherein the composition comprises from 0.1% to 5% by weight of one or more direct dyes of the formula A-L-B, relative to the total weight of the composition.

38. The composition of claim 18, wherein said at least one oxidation base is chosen from para-phenylenediamines, bis(phenyl)alkylenediamines, para-aminophenols, ortho-aminophenols, heterocyclic bases, and the addition salts thereof.

39. The composition of claim 18, wherein said at least one oxidation base is present in an amount ranging from 0.001% to 20% by weight, relative to the total weight of the composition.

40. The composition of claim 18, wherein said at least one oxidation base is present in an amount ranging from 0.005% to 6% by weight, relative to the total weight of the composition.

41. The composition of claim 18, wherein said at least one additional direct dyes is chosen from neutral, acidic, and cationic nitrobenzene dyes; neutral, acidic, and cationic azo direct dyes; neutral, acidic, and cationic quinone dyes; azine direct dyes; triarylmethane direct dyes; indoamine direct dyes; and natural direct dyes.

42. The composition of claim 41, wherein said cation quinone dyes are chosen from anthraquinone direct dyes.

43. The composition of claim 41, wherein said at least one additional direct dyes is present in an amount ranging from 0.001 to 20% by weight, relative to the total weight of the composition.

44. The composition of claim 43, wherein said at least one additional direct dyes is present in an amount ranging from 0.01 to 10% by weight, relative to the total weight of the composition.

45. The composition of claim 18, further comprising at least one oxidation dye precursor chosen from couplers.

46. The composition of claim 45, wherein the coupler is chosen from meta-phenylenediamines, meta-aminophenols, meta-diphenols, naphthalene-based couplers, heterocyclic couplers, and the addition salts thereof.

47. The composition of claim 46, wherein the coupler is chosen from 1,3-dihydroxybenzene, 1,3-dihydroxy-2-methylbenzene, 4-chloro-1,3-dihydroxy-benzene, 2,4-diamino-1-(β-hydroxyethyloxy)benzene, 2-amino-4-(O-hydroxyethylamino)-1-methoxybenzene, 1,3-diaminobenzene, 1,3-bis(2,4-diamino-phenoxy)propane, 3-ureidoaniline, 3-ureido-1-dimethylaminobenzene, sesamol, 1-β-hydroxyethylamino-3,4-methylenedioxybenzene, α-naphthol, 2-methyl-1-naphthol, 6-hydroxyindole, 4-hydroxyindole, 4-hydroxy-N-methylindole, 2-amino-3-hydroxy-pyridine, 6-hydroxybenzomorpholine, 3,5-diamino-2,6-dimethoxypyridine, 1-N-(β-hydroxyethyl)amino-3,4-methylenedioxybenzene, 2,6-bis(β-hydroxyethyl-amino)toluene, and the addition salts thereof.

48. The composition of claim 45, wherein said at least one coupler is present in the composition in an amount ranging from 0.001% to 20% by weight, relative to the total weight of the composition.

49. The composition of claim 45, wherein said at least one coupler is present in the composition in an amount ranging from 0.005% to 6% by weight, relative to the total weight of the composition.

50. The composition of claim 18, further comprising at least one adjuvants chosen from anionic, cationic, nonionic, amphoteric and zwitterionic surfactants and mixtures thereof, anionic, cationic, nonionic, amphoteric and zwitterionic polymers and mixtures thereof, mineral and organic thickeners, antioxidants, penetrating agents, sequestering agents, fragrances, buffers, dispersants, conditioners, film-forming agents, ceramides, preserving agents and opacifiers.

51. The composition of claim 18, further comprising at least one oxidizing agents chosen from hydrogen peroxide, urea peroxide, alkali metal bromates, persalts, peracids and oxidase enzymes.

52. The composition of claim 51, wherein the oxidizing agent is hydrogen peroxide.

53. A process for dyeing keratin fibers, comprising:

providing a direct dye composition comprising a compound of formula A-L-B, wherein A and B are chosen from arylazoimidazolium coloring functional groups, and L is a linker comprising at least one cationic group C, wherein said composition comprises at least one oxidation base, and optionally at least one additional direct dye;

applying said composition to keratin fibers; and leaving the direct dye composition on the keratin fibers for a time period sufficient to allow the fibers to be colored.

54. The process for dyeing keratin fibers of claim 53, wherein said time period is 5 to 60 minutes.

55. The process for dyeing keratin fibers of claim 53, wherein the direct dye composition further comprises at least one oxidation dye precursor.

* * * * *

UNITED STATES PATENT AND TRADEMARK OFFICE
CERTIFICATE OF CORRECTION

PATENT NO.        : 7,282,068 B2                              Page 1 of 10
APPLICATION NO.   : 11/139626
DATED             : October 16, 2007
INVENTOR(S)       : Alain Lagrange et al.

It is certified that error appears in the above-identified patent and that said Letters Patent is hereby corrected as shown below:

- On the title page, item (75), line 2, "Hervé David, "Joinville le Pont (FR);" should read -- Hervé David, La Varenne St. Hilaire (FR); --.

- At cols. 5-6, at lines 1-50, the following figures (II-VI)

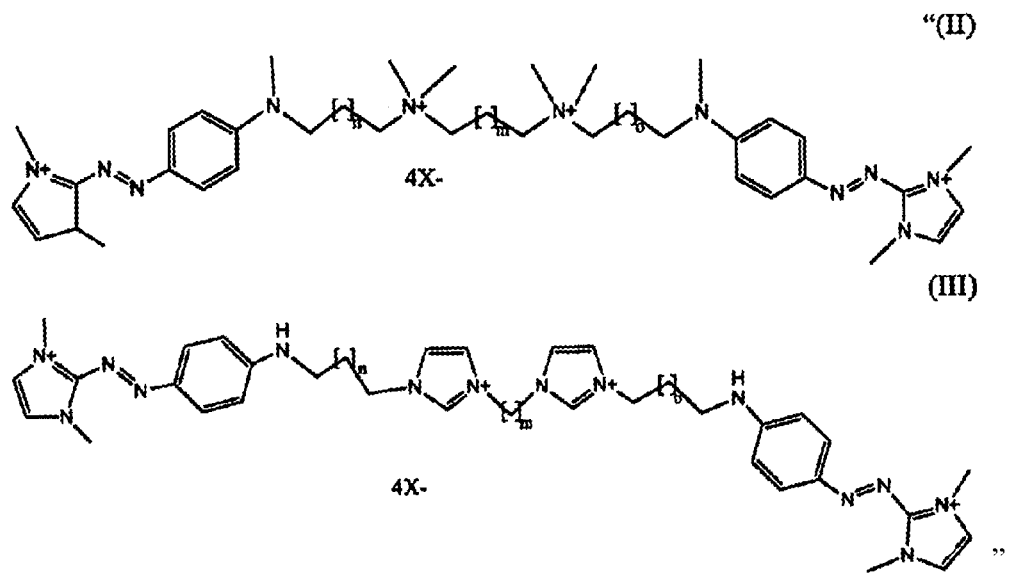

UNITED STATES PATENT AND TRADEMARK OFFICE
CERTIFICATE OF CORRECTION

PATENT NO. : 7,282,068 B2 Page 2 of 10
APPLICATION NO. : 11/139626
DATED : October 16, 2007
INVENTOR(S) : Alain Lagrange et al.

It is certified that error appears in the above-identified patent and that said Letters Patent is hereby corrected as shown below:

should read:

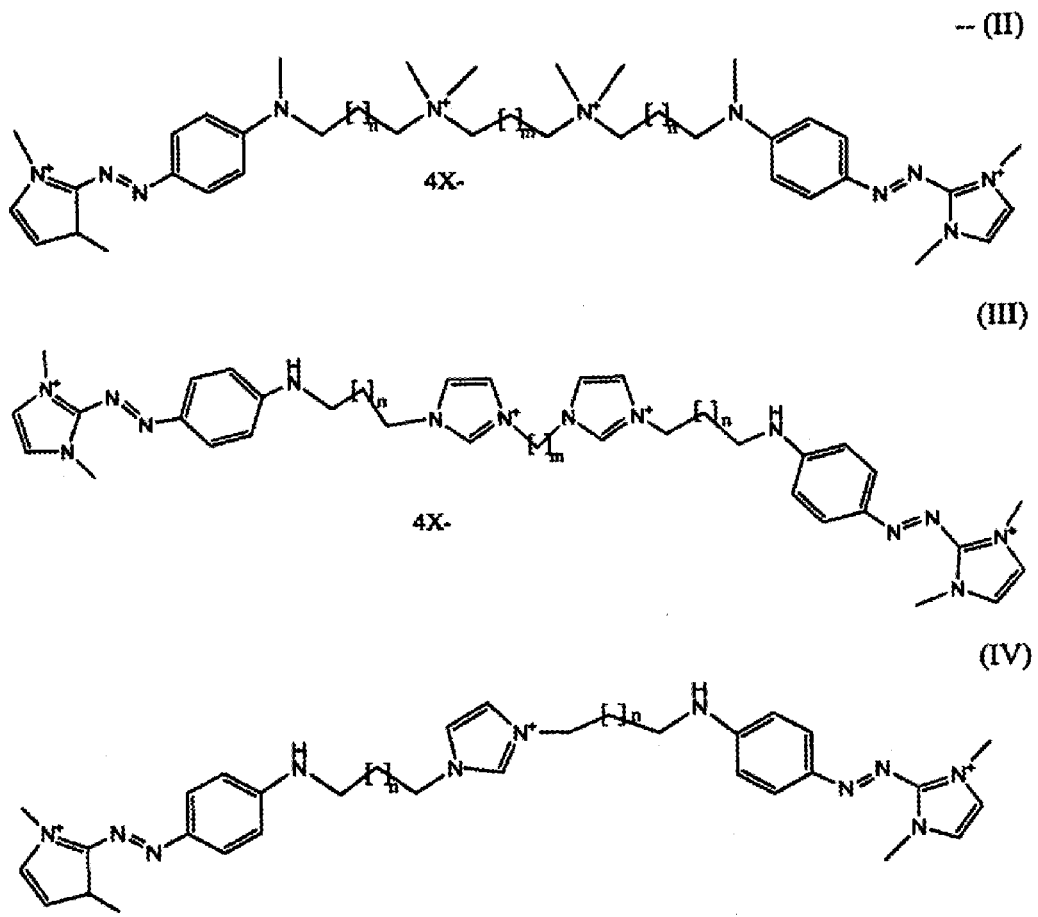

UNITED STATES PATENT AND TRADEMARK OFFICE
CERTIFICATE OF CORRECTION

PATENT NO. : 7,282,068 B2
APPLICATION NO. : 11/139626
DATED : October 16, 2007
INVENTOR(S) : Alain Lagrange et al.

It is certified that error appears in the above-identified patent and that said Letters Patent is hereby corrected as shown below:

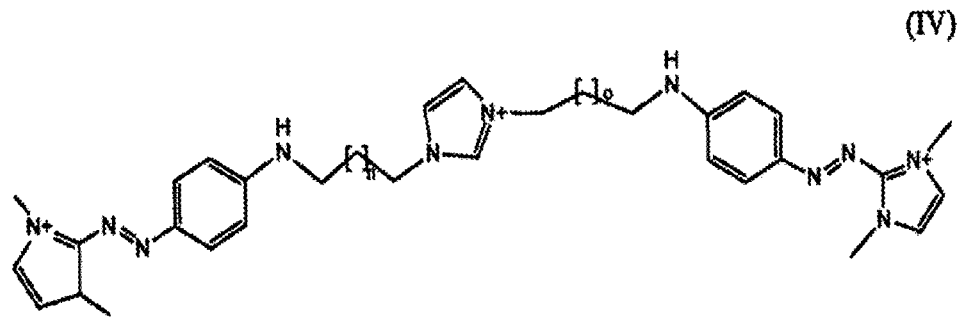

(IV)

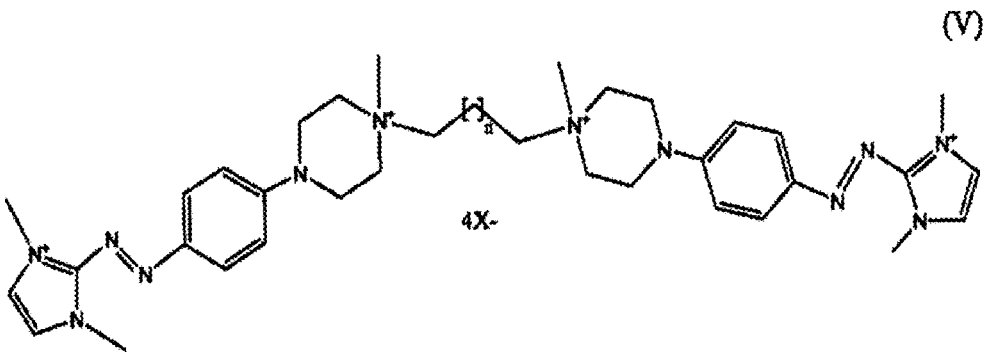

(V)

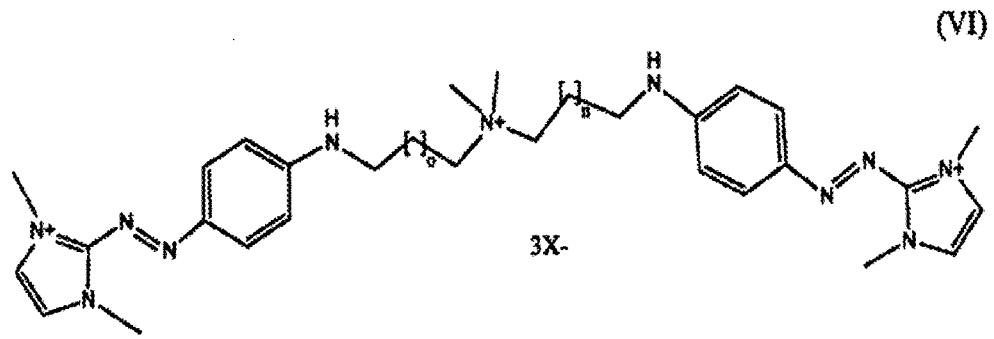

(VI)

UNITED STATES PATENT AND TRADEMARK OFFICE
CERTIFICATE OF CORRECTION

PATENT NO. : 7,282,068 B2  Page 4 of 10
APPLICATION NO. : 11/139626
DATED : October 16, 2007
INVENTOR(S) : Alain Lagrange et al.

It is certified that error appears in the above-identified patent and that said Letters Patent is hereby corrected as shown below:

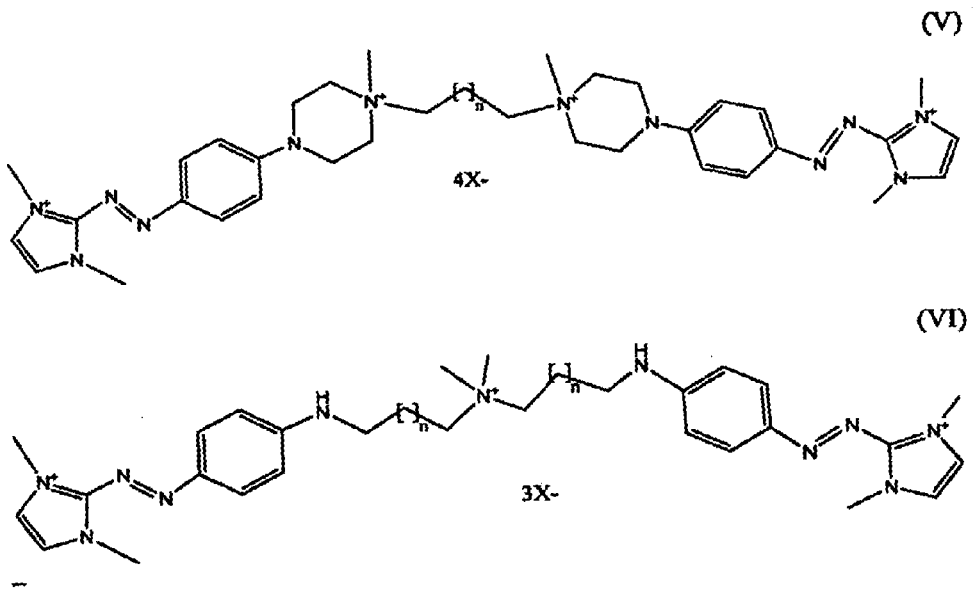

- At claim 15, columns 25-26, lines 43-50 and columns 27-28, lines 1-35, the following figures (I-VI)

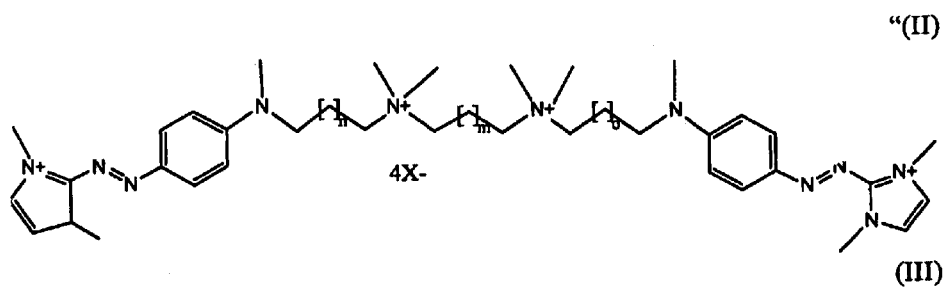

UNITED STATES PATENT AND TRADEMARK OFFICE
CERTIFICATE OF CORRECTION

PATENT NO.        : 7,282,068 B2                                                              Page 5 of 10
APPLICATION NO. : 11/139626
DATED             : October 16, 2007
INVENTOR(S)       : Alain Lagrange et al.

It is certified that error appears in the above-identified patent and that said Letters Patent is hereby corrected as shown below:

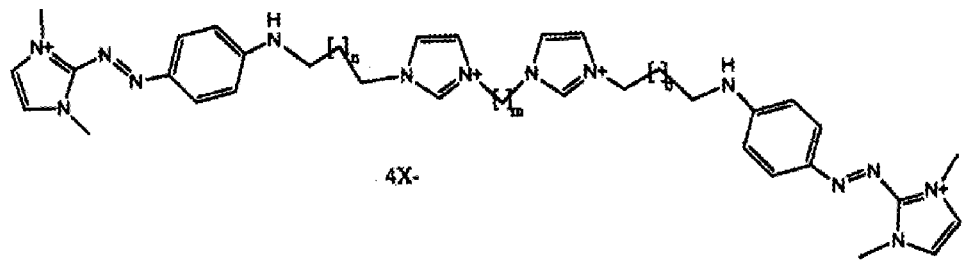

(IV)

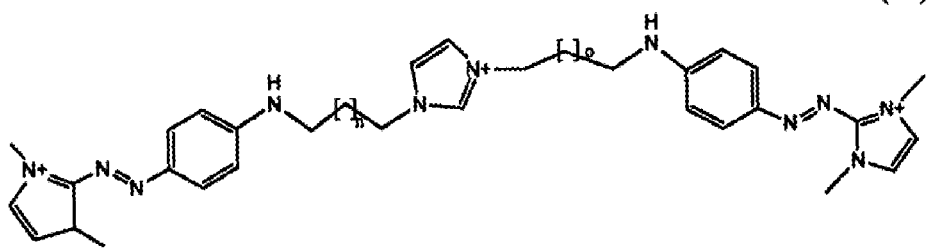

(V)

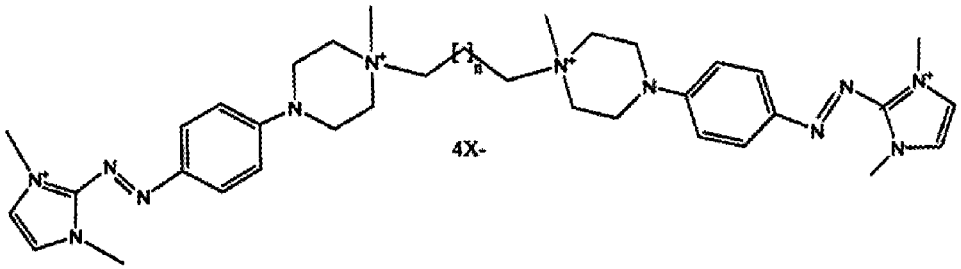

(VI)

UNITED STATES PATENT AND TRADEMARK OFFICE
CERTIFICATE OF CORRECTION

PATENT NO. : 7,282,068 B2  Page 6 of 10
APPLICATION NO. : 11/139626
DATED : October 16, 2007
INVENTOR(S) : Alain Lagrange et al.

It is certified that error appears in the above-identified patent and that said Letters Patent is hereby corrected as shown below:

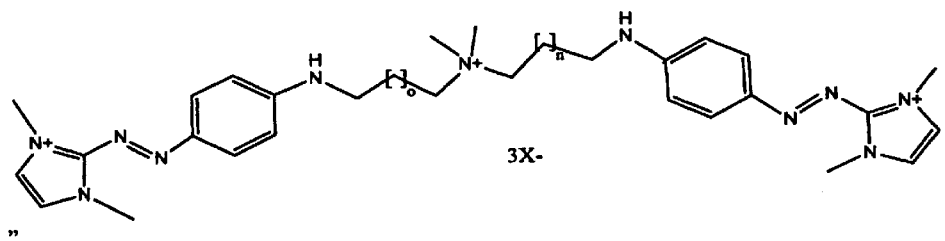

"

should read:

-- (II)

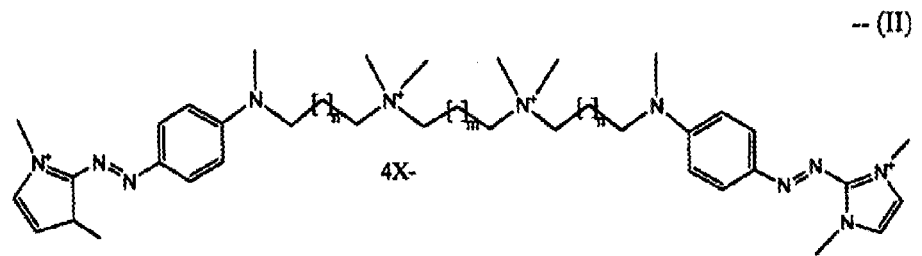

(III)

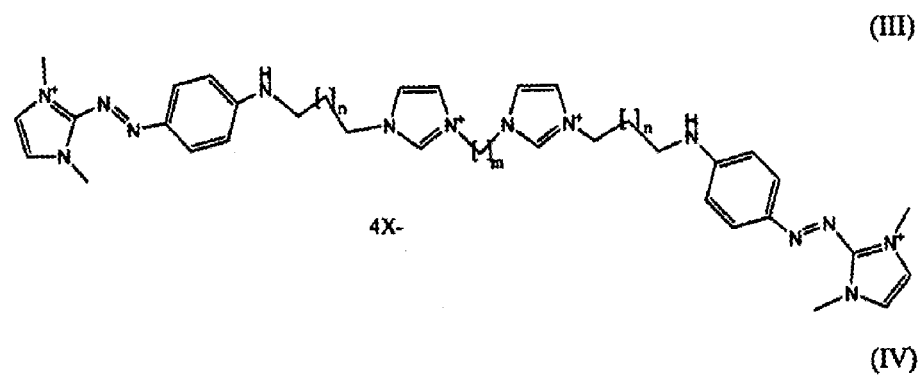

(IV)

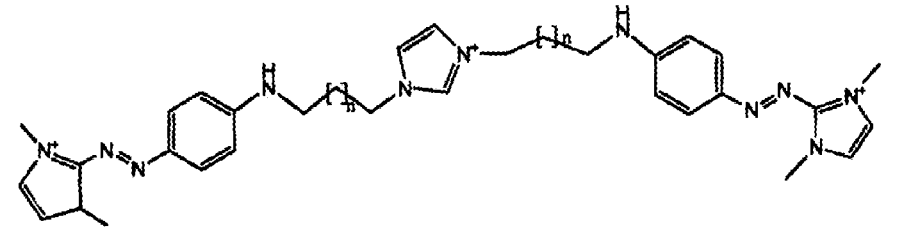

UNITED STATES PATENT AND TRADEMARK OFFICE
CERTIFICATE OF CORRECTION

PATENT NO. : 7,282,068 B2  Page 7 of 10
APPLICATION NO. : 11/139626
DATED : October 16, 2007
INVENTOR(S) : Alain Lagrange et al.

It is certified that error appears in the above-identified patent and that said Letters Patent is hereby corrected as shown below:

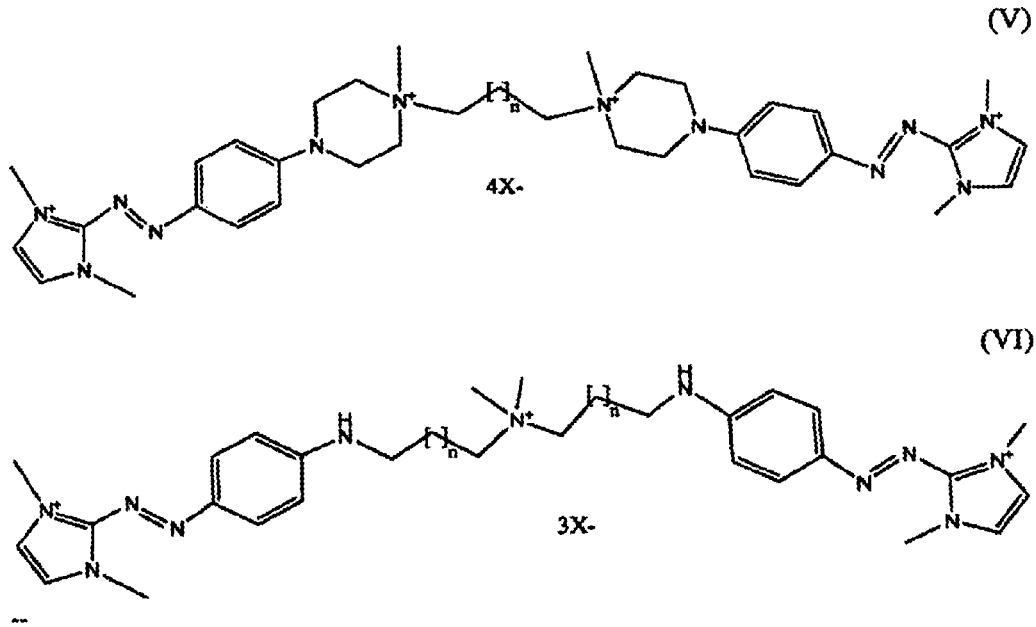

- At claim 32, columns 29-30, lines 43-50 and columns 31-32, lines 1-35, the following figures (I-VI)

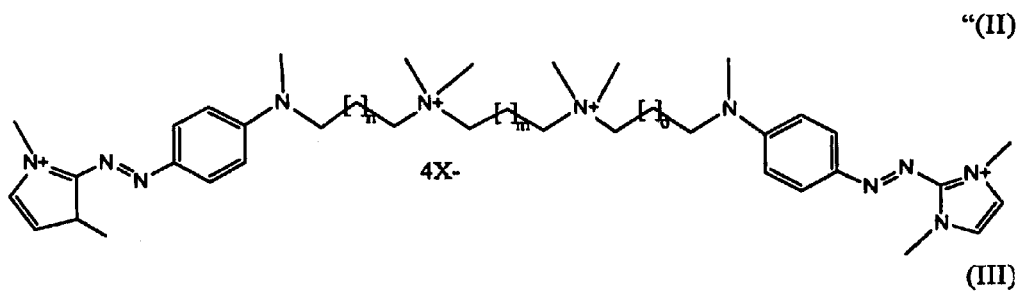

UNITED STATES PATENT AND TRADEMARK OFFICE
CERTIFICATE OF CORRECTION

PATENT NO. : 7,282,068 B2
APPLICATION NO. : 11/139626
DATED : October 16, 2007
INVENTOR(S) : Alain Lagrange et al.

It is certified that error appears in the above-identified patent and that said Letters Patent is hereby corrected as shown below:

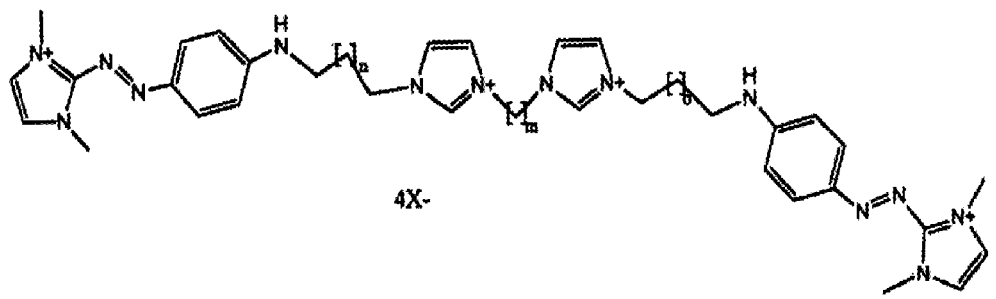

(IV)

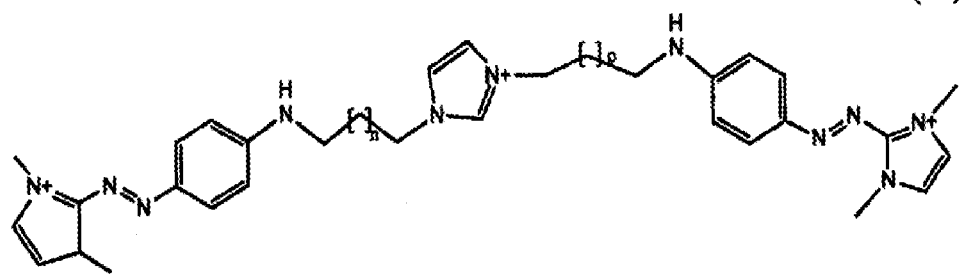

(V)

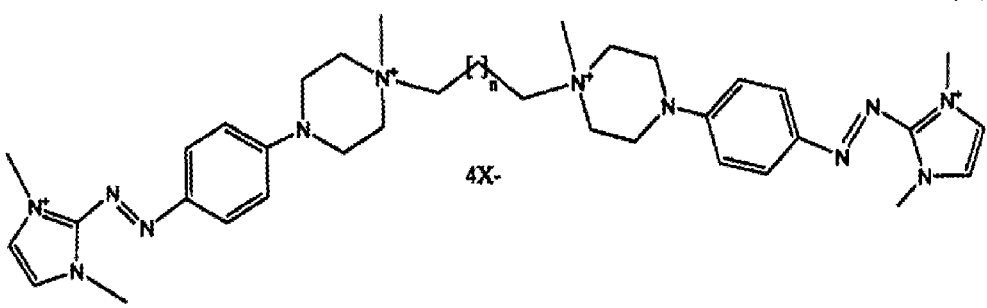

(VI)

UNITED STATES PATENT AND TRADEMARK OFFICE
CERTIFICATE OF CORRECTION

PATENT NO.       : 7,282,068 B2
APPLICATION NO.  : 11/139626
DATED            : October 16, 2007
INVENTOR(S)      : Alain Lagrange et al.

It is certified that error appears in the above-identified patent and that said Letters Patent is hereby corrected as shown below:

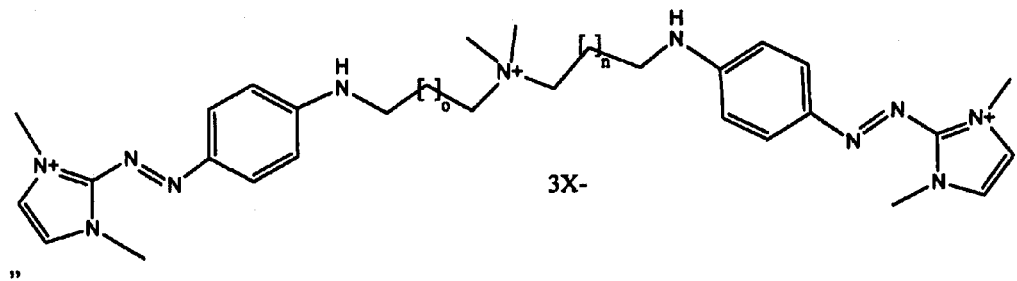

"

should read:

– (II)

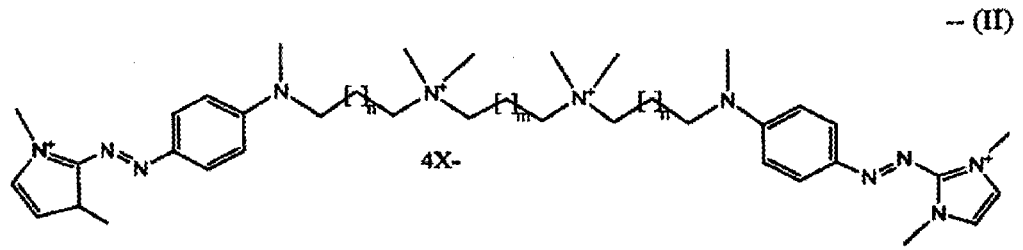

(III)

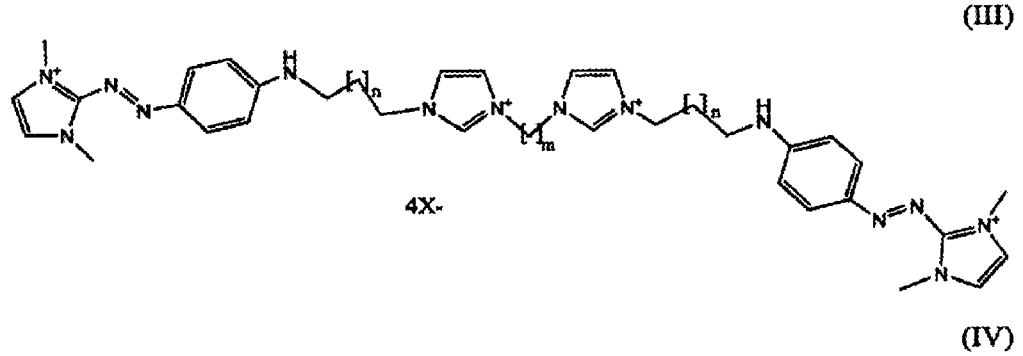

(IV)

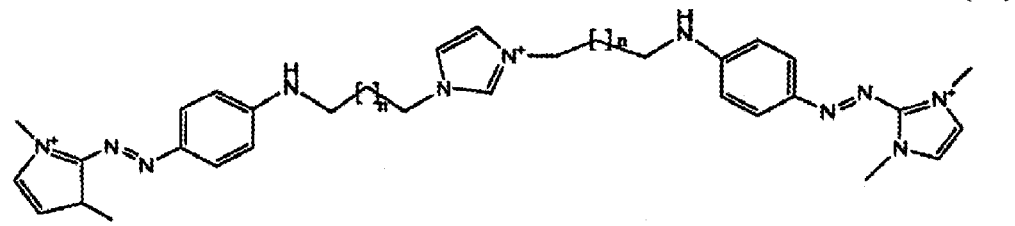

UNITED STATES PATENT AND TRADEMARK OFFICE
CERTIFICATE OF CORRECTION

PATENT NO. : 7,282,068 B2
APPLICATION NO. : 11/139626
DATED : October 16, 2007
INVENTOR(S) : Alain Lagrange et al.

It is certified that error appears in the above-identified patent and that said Letters Patent is hereby corrected as shown below:

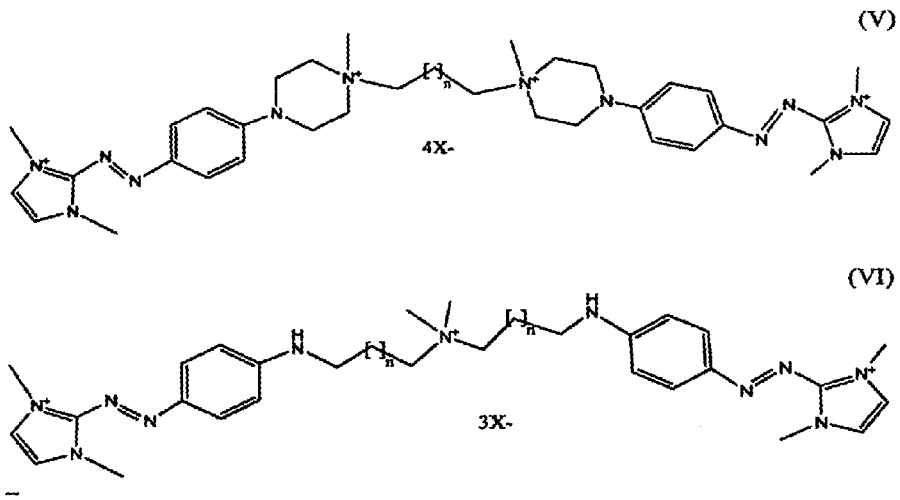

- At claim 47, at col. 32, line 56, "2-amino-4-(O-hydroxyethyl-" should read -- 2-amino-4-(β-hydroxyethyl- --

Signed and Sealed this

Third Day of June, 2008

JON W. DUDAS
*Director of the United States Patent and Trademark Office*